(12) United States Patent
Bornstein

(10) Patent No.: US 8,535,359 B2
(45) Date of Patent: *Sep. 17, 2013

(54) NEAR INFRARED MICROBIAL ELIMINATION LASER SYSTEMS (NIMELS)

(75) Inventor: Eric Bornstein, Natick, MA (US)

(73) Assignee: Nomir Medical Technologies, Inc., Waltham, MA (US)

( * ) Notice: Subject to any disclaimer, the term of this patent is extended or adjusted under 35 U.S.C. 154(b) by 743 days.

This patent is subject to a terminal disclaimer.

(21) Appl. No.: 12/123,023

(22) Filed: May 19, 2008

(65) Prior Publication Data

US 2009/0105790 A1 Apr. 23, 2009

Related U.S. Application Data

(60) Division of application No. 11/930,941, filed on Oct. 31, 2007, now Pat. No. 7,713,294, which is a continuation of application No. PCT/US2006/030434, filed on Aug. 3, 2006, and a continuation-in-part of application No. PCT/US2006/028616, filed on Jul. 21, 2006, and a continuation-in-part of application No. 10/776,106, filed on Feb. 11, 2004, now abandoned, which is a continuation-in-part of application No. 10/649,910, filed on Aug. 26, 2003, now abandoned.

(60) Provisional application No. 60/705,630, filed on Aug. 3, 2005, provisional application No. 60/789,090, filed on Apr. 4, 2006, provisional application No. 60/780,998, filed on Mar. 9, 2006, provisional application No. 60/711,091, filed on Aug. 23, 2005, provisional application No. 60/701,896, filed on Jul. 21, 2005, provisional application No. 60/406,493, filed on Aug. 28, 2002.

(51) Int. Cl.
*A61N 5/06* (2006.01)

(52) U.S. Cl.
USPC ............... 607/88; 606/13; 606/14; 607/89

(58) Field of Classification Search
None
See application file for complete search history.

(56) References Cited

U.S. PATENT DOCUMENTS 6,083,218 A 7/2000 Chou
6,165,205 A 12/2000 Neuberger
(Continued)

FOREIGN PATENT DOCUMENTS

WO WO 2005/055851 A2 6/2005

OTHER PUBLICATIONS

PCT International Preliminary Report on Patentability—(PCT/US2004/004156) Date of Mailing Jun. 17, 2005.

(Continued)

*Primary Examiner* — Bill Thomson
*Assistant Examiner* — Lynsey Crandall
(74) *Attorney, Agent, or Firm* — Foley & Lardner LLP; Matthew L. Fenselau

(57) ABSTRACT

Methods, systems, and apparatus for Near Infrared Microbial Elimination Laser Systems (NIMELS) including use with medical devices are disclosed. The medical devices can be situated in vivo. Suitable medical devices include catheters, stents, artificial joints, and the like. NIMELS methods, systems, and apparatus can apply near infrared radiant energy of certain wavelengths and dosimetries capable of impairing biological contaminants without intolerable risks and/or adverse effects to biological moieties other than a targeted biological contaminant associated with traditional approaches described in the art (e.g., loss of viability, or thermolysis). Lasers including diode lasers may be used for one or more light sources. A delivery assembly can be used to deliver the optical radiation produced by the source(s) produced to an application region that can include patient tissue. Exemplary embodiments utilize light in a range of 850 nm-900 nm and/or 905 nm-945 nm at suitable NIMELS dosimetries.

25 Claims, 22 Drawing Sheets

(56) References Cited

U.S. PATENT DOCUMENTS

| | | |
|---|---|---|
| 6,350,123 B1 | 2/2002 | Rizoiu et al. |
| 6,526,297 B1 | 2/2003 | Merilainen |
| 6,605,080 B1 * | 8/2003 | Altshuler et al. ............. 606/3 |
| 2003/0023172 A1 | 1/2003 | Tromberg et al. |
| 2003/0036685 A1 | 2/2003 | Goodman |
| 2003/0097122 A1 | 5/2003 | Ganz et al. |
| 2004/0171938 A1 | 9/2004 | Grable |
| 2005/0256554 A1 * | 11/2005 | Malak ............................ 607/88 |

OTHER PUBLICATIONS

List of documents submitted to the USPTO in parent U.S. Appl. No. 10/649,910, filed Aug. 26, 2003.

Supplementary European Search Report—(EP 06 80 0750) Date of Mailing Mar. 18, 2009.

* cited by examiner

TREATMENT PROTOCOL

UNDERSIDE OF NIMELS OPTICAL CATHETER CONTROLLER (NOCC)

BLACK LINES REPRESENT OPTICAL DISPERSION FORM EMBEDDED FIBEROPTICS INTO SKIN AROUND CATHETER ENTRY WOUND

NEAR INFRARED MICROBIAL ELIMINATION LASER SYSTEMS (NIMELS)

RELATED APPLICATIONS

This application is a divisional of U.S. application Ser. No. 11/930,941, filed 31 Oct. 2007, which is a continuation of International Application No. PCT/US2006/030434 filed 3 Aug. 2006, which claimed the benefit of U.S. Provisional Application Ser. No. 60/705,630, filed 3 Aug. 2005; and a continuation-in-part of International Application No. PCT/US2006/028616 filed 21 Jul. 2006, which claimed priority to U.S. Provisional Patent Application Ser. No. 60/701,896, filed Jul. 21, 2005; U.S. Provisional Patent Application Ser. No. 60/711,091, filed Aug. 23, 2005; U.S. Provisional Patent Application Ser. No. 60/780,998, filed Mar. 9, 2006; and U.S. Provisional Patent Application Ser. No. 60/789,090, filed Apr. 4, 2006; this application is also a continuation-in-part of U.S. application Ser. No. 10/776,106 filed 11 Feb. 2004, which is a continuation-in-part of U.S. application Ser. No. 10/649,910 filed 28 Aug. 2003, which claimed priority to U.S. Provisional Patent Application No. 60/406,493 filed 28 Aug. 2002; the contents of all of which applications are incorporated herein by reference in their entireties.

This application is also related to U.S. Provisional Application Ser. No. 60/705,630, filed 3 Aug. 2005, entitled "Near Infrared Microbial Elimination Laser (NIMEL) System and Devices Based Thereon," the contents of which are incorporated herein in their entirety by reference, and which is assigned to the assignee of the present application. This application is also related to the following applications, of common assignee as the present application: Near Infrared Microbial Elimination Laser (NIMEL) System," U.S. Provisional Patent Application Ser. No. 60/701,896, filed 21 Jul. 2005; "Near Infrared Microbial Elimination Laser (NIMEL) System," U.S. Provisional Patent Application Ser. No. 60/711,091, filed 23 Aug. 2005; "Method and Apparatus for the Treatment of, and Prevention of Recurrence of Finger and Toenail Infections," U.S. Provisional Patent Application Ser. No. 60/780,998, filed 9 Mar. 2006; and "Method and Device for the Uniform Illumination of NIMELS Optical Energy and Dosimetry to a Biological Containment in a Biological Moiety," U.S. Provisional Patent Application Ser. No. 60/789,090, filed 4 Apr. 2006; all of which applications are incorporated herein in their entirety by reference.

BACKGROUND

1. Field of the Disclosure

The present disclosure relates to methods, systems, and apparatus for selectively reducing the level of a biological contaminant in a target site, including target sites encompassing or partially including one or more medical devices. The present disclosure also encompasses therapeutic modalities, and more particularly, relates to methods, devices, and systems using optical radiation.

2. Background of the Disclosure

Several *E. coli* species and other enterococci are known to have intrinsic and acquired resistance to most antibiotics making them significant nosocomial pathogens in human and animal disease. Boyce, et al., J. Clin. Microbiol. 32(5):114853 (1994); Donskey, et al., N. Engl. J. Med. 343 (26):1925-32 (2000); Landman, et al., J. Antimicrob. Chemother. 40(2):161-70 (1997). Human infections that are caused by enterococci can include endocarditis, bacteremia, urinary tract infection, wound infection, and intra-abdominal and pelvic infections.

For a great number of these infections, the organisms originate from the patient's own intestinal flora, and then spread to cause urinary tract, intra-abdominal, and surgical wound infections. In severe cases, bacteremia may result with subsequent seeding of more distant sites. Whiteside, et al., Am. J. Infect. Control 11(4):125-9 (1983); Patterson, et al., Medicine (Baltimore) 74(4):191-200 (1995); Cooper, et al., Infect. Dis. Clin. Practice 2:332-9. (1993). Recently in the United States, the National Nosocomial Infections Surveillance survey (NNIS) ranked Enterococci from the second to the fourth most common cause of nosocomial infections. Enterococci frequently cause urinary tract infections, bloodstream infections, and wound infections in hospitalized patients.

In addition, enterococci cause 5-15% of all bacterial endocarditis cases. Also, there is reported high prevalence of skin colonization with vancomycin-resistant enterococci that greatly increases the risk of catheter-related sepsis, cross-infection, or blood culture contamination. CDC. National Nosocomial Infections Surveillance (NNIS) System report, Am. J. Infect. Control 26:522-33 (1998); Beezhold, et al., Clin. Infect. Dis. 24(4):704-6 (1997); Tokars, et al., Infect. Control Hosp. Epidemiol. 20(3):171-5 (1999). Of particular interest for the NIMELS laser system are the infectious entities known as cutaneous or wound infections with Enterococci.

Enterococcal infections involve almost any skin surface on the body known to cause skin conditions such as boils, carbuncles, bullous impetigo and scalded skin syndrome. *S. aureus* is also the cause of staphylococcal food poisoning, enteritis, osteomilitis, toxic shock syndrome, endocarditis, meningitis, pneumonia, cystitis, septicemia and post-operative wound infections. Tomi, et al., J. Am. Acad. Dermatol. 53(1):67-72 (2005); Breuer, et al., Br. J. Dermatol. 147(1):55-61 (2002); Ridgeway, et al., J. Bone Joint Surg. Br. 87(6):844-50 (2005). *Staphyloccoccus* infections can be acquired while a patient is in a hospital or long-term care facility.

The confined population and the widespread use of antibiotics have led to the development of antibiotic-resistant strains of *S. aureus*. These strains are called methicillin resistant *staphylococcus aureus* (MRSA). Infections caused by MRSA are frequently resistant to a wide variety of antibiotics and are associated with significantly higher rates of morbidity and mortality, higher costs, and longer hospital stays than infections caused by non-MRSA microorganisms. Risk factors for MRSA infection in the hospital include surgery, prior antibiotic therapy, admission to intensive care, exposure to a MRSA-colonized patient or health care worker, being in the hospital more than 48 hours, and having an indwelling catheter or other medical device that goes through the skin. Hidron, et al., Clin. Infect. Dis. 15; 41(2):159-66 (2005); Hsueh, et al., Int. J. Antimicrob. Agents 26(1):43-49 (2005).

These enterococcal and staphylococcal infections have a huge potential for central venous catheters CVC Infection, and can cause substantial morbidity and mortality in patients. Tomi, et al. (supra). In fact, the data presents that in the United States, 15 million CVC days (i.e., the total number of days of exposure to CVCs by all patients in the selected population during the selected time period) occur in ICUs each year Mermel L. A., Ann. Intern. 132:391-402 (2000). This translates into an average rate of CVC-associated bloodstream infections at 5.3 per 1,000 catheter days in the ICU CDC (supra), or stated another way, approximately 80,000 CVC-associated bloodstream infections occur in ICUs each year in the United States. The attributable cost per infection to the healthcare arena is an estimated $34,508-$56,000 Rello, et al., Am. J. Respir. Crit. Care Med; 162:1027-30 (2000); Dimick, et al., Arch. Surg. 136:229-34 (2001), and the annual cost of caring for patients with CVC-associated BSIs ranges from $296 million to $2.3 billion. Mermel L. A., Ann. Intern. Med. 133:395 (2000).

The importance of fungal infections in the healthcare environment cannot be overstated. As an example, *Candida albicans* is known to the seventh most common pathogen associated with nosocomial infection in ICU patients in hospitals. Fridkin, et al., Clinics In Chest Medicine, 20:(2) (1999). With *C. albicans* the generally accepted therapeutic options for treatment are the polyene class of antifungals (amphotericin), the imidazole class of antifungals, and triazoles. Many of these therapies need to be taken for extended periods of time (with concurrent systemic and organ system danger) and there is much evidence of emergence of antimicrobial-resistant fungal pathogens. When this occurs, the therapeutic options become few and limited.

As an example, there are patients with acquired immunodeficiency syndrome patients, predominantly those with larger exposure to azole therapy or low CD4 counts, that have developed azole-resistant *C. albicans* infections. Johnson, et al., J. Antimicrob. Chemother. 35:103-114 (1995); Maenza, et al., J. Infect. Dis. 173:219-225 (1996). The recent appearance of azole-resistant *C. albicans* in acquired immunodeficiency syndrome patients most likely heralds coming resistance issues in other immuno-compromised patient populations.

These data imply that the escalating use of prophylactic antifungal therapy in highest risk patients for endogenous fungal infections may lead to the increasing frequency of fungal pathogens like *C. krusei*, which have intrinsic azole-resistance, or the even azole resistant *C. glabrata* or *C. albicans*. Maenza, et al., (supra); Beezhold, et al., Clin. Infect. Dis. 24:704-706 (1997); Fridkin, et al., Clin. Microbiol. Rev. 9:499-511 (1996); Johnson, et al., J. Antimicrob. Chemother. 35:103-114 (1995).

Continuing with this ominous trend, data from a 1998 multi-center study of 50 U.S. medical centers, documents that 10% of *C. albicans* isolates from the bloodstream of hospitalized patients were resistant to the antifungal drug fluconazole. Pfaller, et al., Diagn. Microbiol. Infect. Dis. 31:327-332 (1998). The resistant rate ranged from 5% to 15%, depending on the region of the United States, suggesting that local factors, such as amount of azole usage, may play a role in the relative frequency of azole-resistant *C. albicans* infections.

Of particular interest are the infectious entities known as cutaneous Candidiasis. These *Candida* infections involve the skin, and can occupy almost any skin surface on the body. However, the most often occurrences are in warm, moist, or creased areas (such as armpits and groins). Cutaneous candidiasis is extremely common. Huang, et al., Dermatol. Ther. 17(6):517-22 (2004). *Candida* is the most common cause of diaper rash, where it takes advantage of the warm moist conditions inside the diaper. The most common fungus to cause these infections is *Candida albicans*. Gallup, et al., J. Drugs Dermatol. 4(1):29-34 (2005). *Candida* infection is also very common in individuals with diabetes and in the obese. *Candida* can also cause infections of the nail, referred to as onychomycosis, and infections around the corners of the mouth, called angular cheilitis.

Thus, the literature described portends the need for innovative and novel treatments to address these infections.

Traditionally, solid state diode lasers in the visible and near infrared spectrum (e.g., wavelengths of 600 nm to 1100 nm) have been used for a variety of purposes in medicine, dentistry, and veterinary science because of their preferential absorption curve for melanin and hemoglobin in biological systems. Because of the poor absorption in water of near infrared optical energy, the penetration of such radiation in biological tissue is far greater than that of visible or longer infrared wavelengths (e.g., mid-infrared and far infrared). Specifically, near infrared diode laser energy can penetrate biological tissue to about 4 centimeters. In contrast, longer wavelength radiant energy (e.g., that of Er:YAG and $CO_2$ lasers producing mid infrared and far infrared radiation, respectively), has a relatively high water absorption curve and penetrates biological tissue only to from 15 to 75 microns (where 10,000 microns=1 cm). Thus, with radiation from near infrared diode lasers, heat deposition can occur much deeper in biological tissue than for mid-infrared and far infrared wavelengths. Hence, it is more therapeutic for cancer treatment such as laser-interstitial-thermal-therapy for deep tumor ablation or laser-heat-generated-microbial sterilization.

For the destruction of bacterial cells with visible and near infrared diode lasers, the prior art requires the presence of an exogenous chromophore at a site being irradiated and/or a very narrow therapeutic window and opportunity for treatment. Normal human temperature is 37° C., which corresponds to rapid bacterial growth in most bacterial infections. When radiant energy is applied to a biological system with a near infrared diode laser, the temperature of the irradiated area starts to rise immediately, with each 10° C. rise carrying an injurious biological interaction. At 45° C. there is tissue hyperthermia, at 50° C. there is a reduction in enzyme activity and cell immobility, at 60° C. there is denaturation of proteins and collagen with beginning coagulation, at 80° C. there is a permeabilization of cell membranes, and at 100° C. there is vaporization of water and biological matter. In the event of a significant duration of a temperature above 80° C., (5 to 10 seconds in a local site), irreversible harm to healthy cells will result.

Photothermolysis (heat induced lysis) of bacteria with near infrared laser energy, in the prior art, requires a significant temperature increase that may endanger mammalian cells. However, most often it is desired to destroy bacteria thermally, without causing irreversible thermal damage to mammalian cells. Diode lasers have been used to destroy bacteria with visible laser energy (400 nm to 700 nm) in the prior art. The application to a bacterial site of exogenous chromophores has been needed for photodynamic therapy by visible radiation. In the prior art, photodynamic inactivation of bacteria has been achieved when an exogenous chromophore is applied to prokaryotic (microbial) cells and is then irradiated with an appropriate light or laser source. In reference to efforts to preferentially destroy bacteria by generation of radical oxygen species with visible wavelengths coupled to an exogenous chromophore, two studies stand out in the prior art literature (see, e.g., Gibson et al., Clin. Infect. Dis., (16) Suppl 4:S411-3 (1993); and Wilson et al., Oral Microb. Immunol. June; 8(3):182-7 (1993) and Wilson et al., J. Oral. Pathol. Med. September; 22(8):354-7 (1993)).

Therefore, there is a need for improved modalities for the reduction of microbial growth while minimizing damage to mammalian cells.

SUMMARY OF THE DISCLOSURE

The present invention provide methods, systems, and apparatus to selectively target a biological contaminant without intolerable risks and/or intolerable adverse effects on a biological moiety (e.g., a mammalian tissue, cell or biochemical entity/preparations such as a protein preparation) other than the biological contaminant.

The present invention provides method, systems, and apparatus that can apply near infrared radiant energy of certain wavelengths and dosimetries capable of impairing biological contaminants without intolerable risks and/or adverse effects to biological moieties other than a targeted biological contaminant associated with traditional approaches described in the art (e.g., loss of viability, or thermolysis). The methods, systems, and apparatus of the invention at times are hereinafter referred by the acronym NIMELS (i.e., Near Infrared Microbial Elimination Laser System).

In a first aspect, the invention provides a method of reducing the level of a biological contaminant in a target site without intolerable risks and/or intolerable adverse effects to biological moieties (e.g., a mammalian tissue, cell or certain biochemical preparations such as a protein preparation) in/at the given target site other than the targeted biological contaminants, by irradiating the target site with optical radiation of desired wavelength(s), power density level(s), and/or energy density level(s). In certain embodiments, such applied optical radiation may have a wavelength from about 850 nm to about 900 nm, at a NIMELS dosimetry, as described herein. In exemplary embodiments, wavelengths from about 865 nm to about 875 nm are utilized. In further embodiments, such applied radiation may have a wavelength from about 905 nm to about 945 nm at a NIMELS dosimetry. In certain embodiments, such applied optical radiation may have a wavelength from about 925 nm to about 935 nm. In representative non-limiting embodiments exemplified hereinafter, the wavelength employed is 930 nm. Biological contaminants that can be treated reduced and/or eliminated according to the present invention include microorganisms such as, for example, bacteria, fungi, molds, mycoplasmas, protozoa, prions, parasites, viruses, and viral pathogens. Exemplary embodiments, as noted below may employ multiple wavelength ranges including ranges bracketing 870 and 930 nm, respectively.

In a second aspect, the invention provides a method of reducing the level of a biological contaminant in a target site without intolerable risks and/or intolerable adverse effects to biological moieties (e.g., a mammalian tissue, cell or certain biochemical preparations such as a protein preparation) located in/at the given target site other than the targeted biological contaminants, by irradiating the target site with (a) an optical radiation having a wavelength from about 850 nm to about 900 nm; and (b) an optical radiation having a wavelength from about 905 nm to about 945 nm, at NIMELS dosimetries. With respect to this combination approach, and as discussed in more details hereinafter, embodiments of the invention can utilize wavelengths from about 865 nm to about 875 nm. Accordingly, in representative non-limiting embodiments exemplified hereinafter, the wavelength employed is 870 nm. Similarly, with respect to the other wavelength ranges contemplated, the optical radiation of the methods/systems described herein may utilize/produce a wavelength from about 925 nm to about 935 nm and/or a second range, which as a non-limiting example could be about 865 nm to about 875 nm. In representative non-limiting embodiments exemplified hereinafter, the wavelength employed is 930 nm.

In the methods according to this aspect of the invention, irradiation by the wavelength ranges contemplated may be performed independently, in sequence, or essentially concurrently (all of which techniques can utilize pulsed and/or continuous-wave, CW, operation). Optical radiation can be provided for a suitable NIMELS application time (Tn), e.g., of from about 50 to about 450 seconds. Further, the NIMELS dosimetry may adjusted as needed or according to formula or disometyr calculators. For example methods/systems according to the present disclosure may provides an energy density from about 200 J/cm$^2$ to about 700 J/cm$^2$ or an energy density from about 275 J/cm$^2$ to about 500 J/cm$^2$.

In a third aspect, the invention provides a system to implement the methods according to other aspects of the invention, e.g., the first and the second aspect of the invention. Such a system can include a laser oscillator for generating the radiation, a controller for calculating and controlling the dosage of the radiation, and a delivery assembly (system) for transmitting the radiation to the treatment site through an application region. Suitable delivery assemblies/systems can include hollow waveguides, fiber optics, and/or free space/beam optical transmission components. Suitable free space/beam optical transmission components can include collimating lenses and/or aperture stops.

In one form, the system may utilize a two or more solid state diode lasers to function as a dual wavelength near-infrared optical source. The two or more diode lasers may be located in a single housing with a unified control, in exemplary embodiments. The two wavelengths can include emission in two ranges approximating 850 nm to 900 nm and 905 nm to 945 nm. The laser oscillator of the present invention may also be used to emit a single wavelength (or a peak value, e.g., central wavelength) in either one of the ranges encompassed by the invention. In certain embodiments, such a laser may be used to emit radiation substantially within the 865-875 nm and the 925-935 nm ranges as described in more details with respect to the first and the second aspects of the invention. Systems exemplified herein are provided as illustrations of possible embodiments of the invention, e.g., a system devised to emit radiation substantially at 870 nm and at 930 nm; other wavelengths may be produced and utilized.

Systems according to the present invention can include a suitable optical source for each individual wavelength range desired to be produced. For a non-limiting example, a suitable solid stated laser diode, a variable ultra-short pulse laser oscillator, or an ion-doped (e.g., with a suitable rare Earth element) optical fiber or fiber laser may be used. In one form, a suitable near infrared laser can include titanium-doped sapphire. Other suitable laser sources including those with other types of solid state, liquid, or gas gain (active) media may be used within the scope of the present invention.

According to one embodiment of the present invention, a therapeutic system can include an optical radiation generation device adapted to generate optical radiation substantially in a first wavelength range from about 850 nm to about 900 nm, a delivery assembly for causing the optical radiation to be transmitted through an application region, and a controller operatively connected to the optical radiation generation device for controlling the dosage of the radiation transmitted through the application region, such that the time integral of the power density and energy density of the transmitted radiation per unit area is below a predetermined threshold. Also contemplated according to this embodiment of the invention, are therapeutic systems especially adapted to generate optical radiation substantially in a first wavelength range from about 865 nm to about 875 nm.

According to further embodiments, a therapeutic system can include an optical radiation generation device that is configured to generate optical radiation substantially in a second wavelength range from about 905 nm to about 945 nm; in certain embodiments the noted first wavelength range may simultaneously or concurrently/sequentially produced by the optical radiation generation device. Also contemplated according to this embodiment are therapeutic systems especially adapted to generate optical radiation substantially in a first wavelength range from about 925 nm to about 935 nm.

The therapeutic system can further include a delivery assembly (system) for transmitting the optical radiation in the second wavelength range (and where applicable, the first wavelength range) through an application region, and a controller operatively for controlling the optical radiation generation device to selectively generate radiation substantially in the first wavelength range or substantially in the second wavelength range or any combinations thereof.

According to a further embodiment, the controller of the therapeutic system includes a power limiter to control the dosage of the radiation. The controller may further include memory for storing patients' profile and dosimetry calculator for calculating the dosage needed for a particular target site based on the information input by an operator. In one embodiment, the memory may also be used to store information about different types of diseases and the treatment profile, for example, the pattern of the radiation and the dosage of the radiation, associated with a particular application.

The optical radiation can be delivered from the therapeutic system to the application site in different patterns. The radiation can be produced and delivered as continuous wave (CW), or pulsed, or a combination of each. For example, in a single wavelength pattern or in a multi-wavelength (e.g., dual-wavelength) pattern. For a further example, two wavelengths of radiation can be multiplexed (optically combined) or transmitted simultaneously to the same treatment site. Suitable optical combination techniques can be used, including, but not limited to, the use of polarizing beam splitters (combiners), and/or overlapping of focused outputs from suitable mirrors and/or lenses, or other suitable multiplexing/combining techniques. Alternatively, the radiation can be delivered in an alternating pattern, in which the radiation in two wavelengths are alternatively delivered to the same treatment site. An interval between two or more pulses may be selected as desired according to NIMELS techniques of the invention. Each treatment may combine any of these modes of transmission. The intensity distributions of the delivered optical radiation can be selected as desired. Exemplary embodiments utilize top-hat or substantially top-hat (e.g., trapezoidal, etc.) intensity distributions. Other intensity distributions, such as Gaussian may be used.

Other features and advantages of the present invention will be set forth in the detailed description of preferred embodiments that follow, and in part will be apparent from the description or may be learned by practice of the invention. Such features and advantages of the invention will be realized and attained by the systems, methods, and apparatus particularly pointed out in the written description and claims hereof.

BRIEF DESCRIPTION OF THE DRAWINGS

For a fuller understanding of methods, systems, and apparatus of the present invention, reference is made to the following detailed description, which is to be taken with the accompanying drawings, wherein.

DETAILED DESCRIPTION OF THE DISCLOSURE

Figure 1:
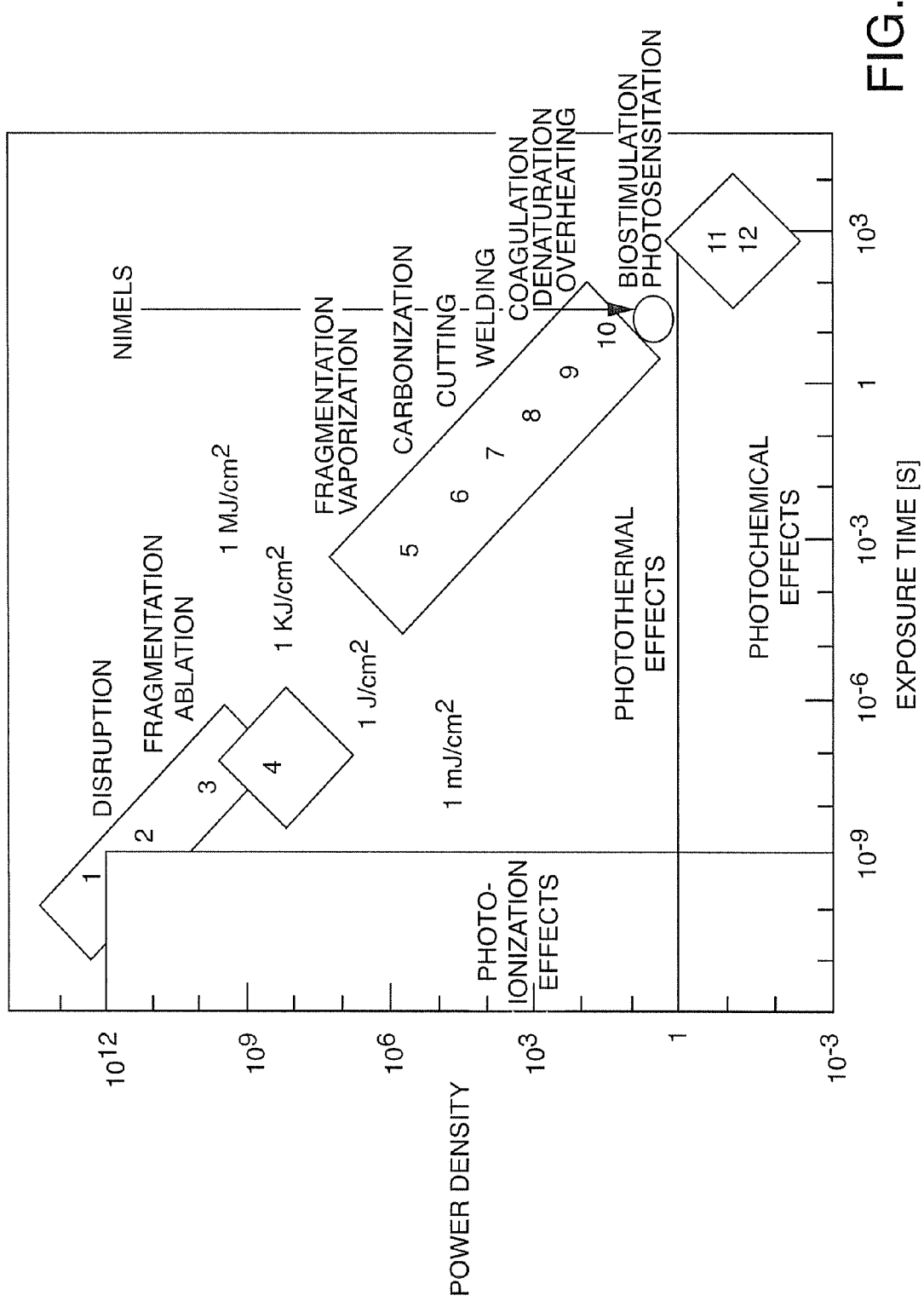
FIG. 1 is a double-logarithmic graph showing power density (ordinate axis) versus irradiation time in seconds (abscissa axis). The main laser-tissue interactions are depicted as a function of different energy density thresholds and parameters. The diagonal lines represent different energy densities showing energy density values exploited according to the present invention (see circled area labeled NIMELS).

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a", "an" and "the" specifically also encompass the plural forms of the terms to which they refer, unless the content clearly dictates otherwise. For example, reference to "a NIMELS wavelength" includes any wavelength within the ranges of the NIMELS wavelengths described, as well as combinations of such wavelengths.

As used herein, unless specifically indicated otherwise, the word "or" is used in the "inclusive" sense of "and/or" and not the "exclusive" sense of "either/or."

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present disclosure pertains, unless otherwise defined. Reference is made herein to various methodologies and materials known to those of skill in the art. Standard reference works setting forth the general principles of microbiology include, Joklik et al., *Zinsser Microbiology*. 20$^{th}$ Ed., Appleton and Lange (Prentice Hall), East Norwalk, Conn. (1992); Greenwood et al., *Medical Microbiology*, 16$^{th}$ Ed., Elsevier Science Ltd., New York (2003); Sambrook et al., *Molecular Cloning: A Laboratory Manual*, 2$^{nd}$ Ed., Cold Spring Harbor Laboratory Press, New York, N.Y. (1989); Kaufman et al., Eds., *Handbook of Molecular and Cellular Methods in Biology in Medicine*, CRC Press, Boca Raton, Fla. (1995); standard reference works setting forth the general principles of pharmacology include Goodman and Gilman's *The Pharmacological Basis of Therapeutics*, 10$^{th}$, Ed., McGraw Hill Companies Inc., New York, N.Y. (2001); and, standard dermatology principles may be found in Habif et al., *Skin Disease, Diagnosis and Treatment*, 1$^{st}$ Ed., Mosby, Inc., St. Louis, Mo. (2001); the entire teachings of all of which are incorporated herein by reference.

The present disclosure provides methods, systems, and apparatus to apply near infrared radiant energy of certain wavelengths and at a certain dosimetries as discussed herein capable of impairing targeted biological contaminants with minimal risks to biological moieties other than the targeted biological contaminant(s). Such methods and devices/systems for example do not generate or rely on impermissible increases in temperatures (i.e., heat) associated with traditional approaches described in the art.

Near infrared radiant energy has been used in the literature as optical tweezers (Ashkin et al., Nature 330:769-771 (1987) the entire teachings of which are incorporated herein by reference) used to manipulate and control biological objects for a variety of applications for which it was desirable to preserve the viability of the cells manipulated. Many reported that the use of near infrared radiation as tweezers was associated with "opticution" or simply the undesired cell impairment (as measured for example by a quantifiable decrease in viability and proliferation) (Ashkin and Dziedzic, Ber. Bunsenges., Phys. Chem. 93:254-260 (1989) the entire teachings of which are incorporated herein by reference). In an effort of optimize optical tweezers that would not hamper the viability of the cells led to the discovery that the action spectrum for photodamage exhibit maxima at 870 and 930 nm (Neuman et al., Biophys. J. 77:2856-2863 (1999) the entire teachings of which are incorporated herein by reference). Similar data in Chinese Hamster Ovary ("CHO") cells (see, e.g., Liang et al., Biophys. J. 70:1529-1533 (1996)) led investigators to believe that the wavelength dependence of photodamage seen in prokaryotic cells was shared by eukaryotic cells as well (Neuman et al., Biophys. J. 77:2856-2863 (1999) the entire teachings of which are incorporated herein by reference). The consensus in the literature thus, has been that near infrared radiation having wavelengths approximating or coinciding with identified maxima at 870 and 900 nm causes cell damage in prokaryotic (e.g., bacteria) and in eukaryotic (e.g., CHO) cells.

More probing studies (exemplified hereinafter) using radiation approximating and coinciding with the 870 and 900 maxima, has led to the elucidation of optical parameters (i.e., wavelength, power density, energy density, and duration of exposure) associated with a remarkable differential effect on targeted sites (e.g. cells). Using such dosimetry parameters it is now possible to use near infrared radiation to target biological contaminants while effecting other biological moieties only marginally, if at all. As it can be easily appreciated, such a discovery has many useful practical applications.

More specifically, it has been found that within certain dosimetry parameters, energy of a wavelength in the ranges of from about 905 nm to about 945 nm is suitable to specifically target biological contaminants in a target site without intolerable risks and/or intolerable adverse effects to biological moieties in a given target site other than the targeted biological contaminants.

Accordingly, in a first aspect, the disclosure provides a method of reducing the level of a biological contaminant in a target site without intolerable risks and/or intolerable adverse effects to biological moieties in a given target site other than the targeted biological contaminants (e.g., a mammalian tissue, cell or certain biochemical preparations such as a protein preparation), by irradiating the target site with an optical radiation having a wavelength from about 905 nm to about 945 nm. In certain embodiments the optical radiation may have a wavelength from about 925 nm to about 935 nm. In representative non-limiting embodiments exemplified hereinafter, the wavelength employed is 930 nm. The target site can include a medical device, which may be positioned in vivo, as described below in further detail.

It has also been found that the effects obtained by irradiating a target site with an optical radiation having a wavelength from about 905 nm to about 945 nm may be augmented by also irradiating with at least one additional optical radiation with a wavelength from about 865 nm to 875 nm at a NIMELS dosimetry. As evidenced herein, the combined irradiation further enhances the effect of the radiation in the 905-945 nm range by reducing the total energy and density required to obtain the desired differential effect on the treated target site. This finding is particularly significant because it translates in a reduction of the radiation in the 905-930 nm range required to obtain the desired effect. As a result, this combined irradiation approach has the additional benefit of further minimizing intolerable risks and/or intolerable adverse effects to biological moieties other than the targeted biological contaminants.

Such synergy has been found when target sites were subjected to two wavelengths of (a) from about 850 nm to 900 nm and of (b) from about 905 nm to about 945 nm. In certain representative and non-limiting embodiments exemplified herein, it has been found that, at NIMELS dosimetries, irradiation with a wavelength in the 865-875 nm range enhances the effect of irradiation with a wavelength in the 925-935 nm range. In certain embodiments, the target site was exposed to radiations with $\lambda=870$ and $\lambda=930$ nm with a concomitant reduction of the required total energy and density.

NIMELS wavelengths as described above (e.g., 850-900 nm, and 905-945 nm), may be used to irradiate the target site independently, in sequence, and/or essentially concurrently.

Without wishing to be bound by any theory and not intending to limit any aspect of the disclosure by any theory as to the underlying mechanisms responsible for the phenomena observed, it is postulated that the wavelengths irradiated according to the present methods and systems are absorbed by intracellular endogenous chromophores of prokaryotic and eukaryotic cells, and by the lipid bilayer in the cell membrane. It is further postulated that perhaps bacterial damage may be mediated via toxic singlet oxygen and/or other reactive oxygen species.

It will be understood that intracellular endogenous chromophores of prokaryotic and eukaryotic cells are lipid bilayers (plasma membranes and mitochondrial membranes) that contain large amounts of protein, cytochrome, and enzymatic inclusions, and that the lipid bilayers of the contaminants and moieties targeted by the present invention will have protein/lipid rations of >1. Stated another way, none of the target membranes of the present invention in the contaminant or moiety contain greater than 49.99% lipid by dry weight.

As used herein, the expression "reducing the level of a biological contaminant" is intended to mean a reduction in the level of at least one active biological contaminant found in the target site being treated according to the present disclosure. Empirically, a reduction of the level of a biological contaminant is quantifiably as a reduction of the viability of a biological contaminant in a target site (e.g., by hampering the viability of the subject biological contaminant and/or its ability to grow and/or divide). One of skills in the arts will appreciate that the expression "reduction of levels of a biological contaminant" encompasses any reduction and need not be a 100% reduction. In certain embodiments in fact, the viability of a given biological contaminant may only be reduced in part to allow other events to take place (e.g., allow a patient's immune system to react to a given infection, or allow other concomitant treatments—e.g., a systemic antibiotic treatment—to address a given infection). In certain instances it has been found that a given biological contaminant's susceptibility to antimicrobial may be enhanced following treatment according to the disclosure. In particular embodiments, MRSA strains were found to be more susceptible to antibiotics as a result of treatments according to the disclosure.

As used herein, the term "biological contaminant" is intended to mean a contaminant that, upon direct or indirect contact with the target site, is capable of undesired and/or deleterious effect(s) on the target site (e.g., an infected tissue or organ of a patient) or upon a mammal in proximity of the target site (e.g., in the case of a cell, tissue, or organ transplanted in a recipient, or in the case of a device used on a patient). Biological contaminants according to the disclosure are microorganisms such as, for example, bacteria, fungi, molds, mycoplasmas, protozoa, prions, parasites, viruses, and viral pathogens known to those of skill in the art to generally be found in the target sites according to the disclosure. One of skill in the art will appreciate that the methods and system/devices of the disclosure may be used in conjunction with a variety of biological contaminants known in the literature at large (see, e.g., Joklik et al., (supra); and Greenwood et al., (supra)).

As used herein, the term "endogenous chromophores of biological contaminants that are bacteria" is intended to mean cell membranes with a protein/lipid ratio of >1.

As used herein, the term "endogenous chromophores of biological contaminants that are fungi" is intended to mean cell membranes and mitochondrial membranes with a protein/lipid ratio of >1.

The following lists are provided solely for the purpose of illustrating the broad scope of microorganisms which may be targeted according to the methods and devices/systems of the disclosure and are not intended to limit the scope of the applicability of the disclosure in any manner whatsoever.

Accordingly, illustrative non-limiting examples of biological contaminants include any bacteria, such as, for example, *Escherichia, Enterobacter, Bacillus, Campylobacter, Corynebacterium, Klebsiella, Treponema, Vibrio, Streptococcus* and *Staphylococcus*.

To further illustrate, biological contaminants contemplated include any fungus, such as, for example, *Candida, Aspergillus, Cryptococcus*, various dermatophytes (e.g., *Trichophyton, Microsporum*, and *Epidermophyton*), *Coccidioides, Histoplasma, Blastomyces*. Parasites may also be targeted biological contaminants such as *Trypanosoma* and malarial parasites, including *Plasmodium* species, as well as molds; mycoplasmas; prions; and viruses, such as human immunodeficiency viruses and other retroviruses, herpes viruses, parvoviruses, filoviruses, circoviruses, paramyxoviruses, cytomegaloviruses, hepatitis viruses (including hepatitis B and hepatitis C), pox viruses, toga viruses, Epstein-Barr virus and parvoviruses.

It will be understood that the target site to be irradiated need not be already infected with a biological contaminant. Indeed, the methods of the disclosure may be used "prophylactically," prior to infection (e.g., to prevent it). Exemplary embodiments may be used on medical devices such as catheters, artificial joints, etc.

In certain instances, irradiation may be palliative as well as prophylactic. Hence, the methods of the disclosure may be used to irradiate a tissue or tissues for a therapeutically effective amount of time for treating or alleviating the symptoms of an infection. The expression "treating or alleviating" means reducing, preventing, and/or reversing the symptoms of the individual treated according to the disclosure, as compared to the symptoms of an individual receiving no such treatment.

A practitioner will appreciate that the methods described herein are to be used in concomitance with continuous clinical evaluations by a skilled practitioner (physician or veterinarian) to determine subsequent therapy. Hence, following treatment the practitioners will evaluate any improvement in the treatment of the underlying condition according to standard methodologies. Such evaluation will aid and inform in evaluating whether to increase, reduce or continue a particular treatment dose, mode of irradiation, and adjunctive treatments etc.

As discussed throughout the description of the disclosure, the term "target site" denotes any cell, tissue, organ, object or solution which may become contaminated with a biological contaminant. Thus, the target site may be a cell, tissue or organ of a mammal which is or may become infected with a biological contaminant posing a risk to a mammal, e.g., tissue surrounding an implanted (in vivo) medical device. In the alternative, the target site may be a cell, tissue or organ of a mammal which is or may become infected with a biological contaminant posing a risk to a mammal in proximity of the target site (e.g., such as for example in the case of a cell, tissue, or organ transplanted in a recipient mammal, or in the case of a device used on a mammal). Foremost among such mammals are humans, although the disclosure is not intended to be so limited, and is applicable to veterinary uses. Thus, in accordance with the disclosure, "mammals" or "mammal in need" or "patient" include humans as well as non-human mammals, particularly domesticated animals including, without limitation, cats, dogs, and horses. The target site may include a medical device, such as a catheter, stent, artificial joint, etc.

One of skill in the art will appreciate that the disclosure is useful in conjunction with a variety of diseases caused by or otherwise associated with any microbial, fungal, and viral infection (see in general Harrison's, *Principles of Internal Medicine*, 13$^{th}$ Ed., McGraw Hill, New York (1994) the entire teachings of which are incorporated herein by reference). In certain embodiments, the methods and the system according to the disclosure may be used in concomitance with traditional therapeutic approaches available in the art (see, e.g., Goodman and Gilman's (supra)) to treat an infection by the administration of known antimicrobial agents compositions. The terms "antimicrobial composition", "antimicrobial agent" refer to the compounds and combinations thereof that may be administered to an animal or human and which inhibit the proliferation of a microbial infection (e.g., antibacterial, antifungal and antiviral).

The wide breath of applications contemplated include for example a variety of dermatological, podiatric, pediatric, and general medicine to mention but a few.

A plethora of dermatological conditions may be treated according to the methods, devices/systems of the disclosure (see, for example, Habif et al. (supra)). Without wishing to be bound to the specific infections listed, the disclosure for example may be used to treat *Corynebacteria* infections which may cause erythrasma, trichomycosis axillaries, and pitted keratolysis; *Staphylococcus* infections which may cause impetigo, ecthyma and folliculitis, and *Streptococcus* infections that may cause impetigo and erysipelas. Erythrasma is a superficial skin infection caused by *Corynebacteria* that commonly occurs in intertriginous spaces. Impetigo is a common infection in children that may also occur in adults. It is generally caused by either *Staphylococcus aureus* or *Streptococcus*. Ecthyma occurs in debilitated persons, such as patients with poorly controlled diabetes, and is generally caused by the same organisms that cause impetigo. Patients with folliculitis present with yellowish pustules at the base of hairs, particularly on the scalp, back, legs and arms. Furuncles, or boils, are more aggressive forms of folliculitis. Erysipelas presents acutely as marked redness, pain and swelling in the affected area. The illness is generally believed to be caused by beta-hemolytic Streptococci. See, for example, Trueb et al., Pediatr Dermatol 1994; 11:35-8 (1994); Trubo et al., Patient Care 31(6):78-94 (1997); Chartier et al., Int. J. Dermatol. 35:779-81 (1996); and Eriksson et al., Clin. Infect. Dis. 23:1091-8 (1996) the entire teachings of which are incorporated herein by reference.

Similarly, fungus and yeast may infect skin tissues causing a variety of conditions (dermatomycoses) which may be addressed according to the disclosure including, for example, tinea capitis, tinea barbae, tinea cruris, tinea manus, tinea pedis and tinea unguium (see, onychomycosis discussed infra) (see, Ansari et al., Lower Extremity Wounds 4(2):74-87 (2005); Zaias, et al., J. Fam. Pract. 42:513-8 (1996), Drake et al., J. Am. Acad. Dermatol. 34(2 Pt 1):282-6 (1996); Graham et al., J. Am. Acad. Dermatol. 34(2 Pt 1):287-9 (1996); Egawa et al., Skin Research and Tech. 12:126-132 (2005); and Hay, Dermatol. Clin. 14:113-24 (1996) the entire teachings of which are incorporated herein by reference). Candidal pathogen based infections will generally occur in moist areas, such as, skinfolds and diaper area. Cutaneous wounds that are caused by wood splinters or thorns may result in sporotrichosis (see, Kovacs et al., Postgrad Med 98(6):61-2, 68-9, 73-5 (1995) the entire teachings of which are incorporated herein by reference). *Candida albicans* and *Trichophyton, Epidermophyton, Microsporum, Aspargillum*, and *Malassezia* species are the common infecting organisms (see, Masri-Fridling, Dermatol. Clin. 14:33-40 (1996) the entire teachings of which are incorporated herein by reference).

HPV (Human papillomavirus) may also cause skin infections that may manifest clinically as different types of warts, depending on the surface infected and its comparative moisture. Commonly occurring warts include common warts, plantar warts, juvenile warts and condylomata. No standard and routinely effective treatment for warts exists to date (Sterling, Practitioner 239:44-7 (1995) the entire teachings of which are incorporated herein by reference).

As exemplified hereinafter, the disclosure may be used for the treatment of onychomycosis i.e., a disease (e.g., a fungal infection) of the nail plate on the hands or feet. As used herein, reference to a "nail" includes reference to one, or some, or all parts of the nail complex, including the nail plate (the stratum corneum unguis, which is the horny compact outer layer of the nail, i.e., visible part of the nail), the nail bed (the modified area of the epidermis beneath the nail plate, over which the nail plate slides as it grows), the cuticle (the tissue that overlaps the nail plate and rims the base of the nail), the nail folds (the skin folds that frame and support the nail on three sides), the lunula (the whitish half-moon at the base of the nail), the matrix (the hidden part of the nail under the cuticle), and the hyponychium (the thickened epidermis underneath the free distal end of a nail) and the nail matrix. Nails grow from the matrix. Nails are composed largely of keratin, a hardened protein (that is also ill skin and hair). As new cells grow in the matrix, the older cells are pushed out, compacted and take on the familiar flattened, hardened form of a fingernail or toenail.

Nail fungal disease may be caused by the three genera of dermatophytes, *Trichophyton, Microsporum, Epidermophyton*, the yeast *Candida*, (the most prevalent of which being *C. albicans*, and/or or moulds such as *Scopulariopsis brevicaulis, Fusarium* spp., *Aspergillis* spp., *Alternaria, Acrenionium, Scytalidinum dimidiatum* (*Hendersonula toruloides*), *Scytalidinium hyalinum*. Onychomycosis may affect one or more toenails and/or fingernails and most often involves the great toenail or the little toenail. It can present in one or several different patterns such as lateral onychomycosis (a white or yellow opaque streak appears at one side of the nail), subungual hyperkeratosis (scaling occurs under the nail), and distal onycholysis (when the end of the nail lifts upwards). Common clinical findings include crumbling of the free edge (e.g., superficial white onychomycosis), flaky white patches and pits appear on the top of the nail plate (e.g., proximal onychomycosis), yellow spots appear in the half-moon (lunula), and the complete destruction of the nail (see Sehgal and Jain, Inter. J. of Dermatol. 39:241-249 (2000); Hay, JEADV 19 (Suppl. 1.):1-7 (2005); Warshaw et al., Inter. J. of Dermatol. 44:785-788 (2005); Sigureirsson et al., J. of Dermatol. Treatmt. 17:38-44 (2006); Rodgers et al., Amer. Fam. Phys.; see, at http://www.aafp.org/afp/20010215/663.html));

Lateur, J. of Cosmet. Dermatol. 5:171-177 (2006) the entire teachings of which are incorporated herein by reference).

It will be readily appreciated that treatment according to the disclosure also provides modalities to address many known clinical events associated with onychomycosis and tinea corporis. The absence of effective therapy for many patients affected by onychomycosis has been found to have a profound impact on the patients' quality of life leading to considerable psychological and psychosocial consequences (see, e.g., Elewski et al., Int. J. Dermatol. 36:754-756 (1997) the entire teachings of which are incorporated herein by reference). Treatment according to the instant disclosure thus, provide a much needed relief from the literature-recognized impact these diseases have on self-image and overall life quality.

Reports in the literature have also confirmed that fungal infections (e.g., onychomycosis) is a risk factor for bacterial tissue infections including infections such as for example acute bacterial cellulitis (see, e.g., Roujeau et al., Dermatology 209:301-307 (2004) the entire teachings of which are incorporated herein by reference). Treatment of fungal infections as described herein therefore provides a novel approach to curb secondary or concomitant infections.

It has been recognized that the significance of onychomycosis and tinea corporis in the diabetic patient may lead to infections, especially bacterial sepsis which may turn into a life-threatening problem given the susceptibility and propensity of diabetic patients to secondary infections at large (see, e.g., Rich, J. Am. Acad. Dermatol. 35:S10-12 (1996) the entire teachings of which are incorporated herein by reference). In patients with labile diabetes, recurrent candidiasis can result in *candida sepsis* and ultimately may also lead to *candida paronchia* further complicating the nail dystrophy from long standing onychomycosis (see, e.g., Millikan et al., Int. J. Dermatol. 38(2):13-16 (1999) the entire teachings of which are incorporated herein by reference).

Numerous nails that are chronically infected with a pathogen often also suffer from chronic or acute paronychia (see, e.g., Rockwell, American Med. Physic. 63(6):1113-1116 (2001); and Grover et al., Dermatol. Surg. 32:393-399 (2006) the entire teachings of which are incorporated herein by reference). Chronic paronychias are localized, superficial infections of the perionychium (epidermis bordering the nails). Paronychial infections develop when a disruption occurs between the seal of the proximal nail fold and the nail plate that allows a portal of entry for invading organisms. Chronic paronychia is generally nonsuppurative and is a difficult disease to treat. Chronic paronychia as a rule, causes swollen, red, tender and boggy nail folds where the symptoms of the disease present for six weeks or longer and are concominent with long term onychomycosis. The disease causing pathogen in these cases typically is a *Candida* species.

In accordance with some embodiments, the methods and devices/systems of the disclosure may be used in conjunction with the administration of a pharmaceutically active compound and/or a composition containing a pharmaceutically active compound. Such administration may be systemic or topical. Various such antifungal pharmaceutically active compounds and compositions suitable for systemic (e.g., orally or by parenteral administration) or topical (e.g., ointments, creams, sprays, gels, lotions and pastes) are known in the art. See, for example, terbinafine as described in e.g., U.S. Pat. Nos. 4,755,534; 6,121,314; 4,680,291; 5,681,849; 5,856,355; 6,005,001, and itraconazole as described in e.g., U.S. Pat. Nos. 5,633,015; 4,727,064; 5,707,975; the entire teachings of which are incorporated herein by reference.

As illustrated infra, it has been found that antibiotic resistant bacteria may be effectively treated according to the methods of the disclosure. In addition, it has been found that the methods of the disclosure may be used to augment traditional approaches to be used in combination with, in lieu of, or even serially as effective therapeutic approaches. Accordingly, the disclosure may be combined with antibiotic treatment. The term "antibiotic" includes, but is not limited to, β-lactams penicillins and cephalosporins), vancomycins, bacitracins, macrolides (erythromycins), ketolides (telithromycin), lincosamides (clindomycin), chloramphenicols, tetracyclines, aminoglycosides (gentamicins), amphotericns, cefazolins, clindamycins, mupirocins, sulfonamides and trimethoprim, rifampicins, metronidazoles, quinolones, novobiocins, polymixins, oxazolidinone class (e.g., linezolid), glycylcyclines (e.g., tigecycline), cyclic lipopeptides (e.g., daptomycin), pleuromutilins (e.g., retapamulin) and gramicidins and the like and any salts or variants thereof. It also understood that it is within the scope of the present disclosure that the tetracyclines include, but are not limited to, immunocycline, chlortetracycline, oxytetracycline, demeclocycline, methacycline, doxycycline and minocycline and the like. It is also further understood that it is within the scope of the present disclosure that aminoglycoside antibiotics include, but are not limited to, gentamicin, amikacin and neomycin and the like.

Other known approaches to the treatment of microbial infections contemplated in conjunction with the methods, devices, and systems described herein include the use of suitable medical dressings. The term "medical dressing" as used herein refers to any covering, protective or supportive, for diseased or injured parts of the skin, or internal organs of a human or animal. The dressing can be, but is not limited to, an absorbent dressing such as a gauze, a sterilized gauze or absorbent cotton, an antiseptic dressing permeated with an antiseptic solution to delay or prevent the onset of an infection, a dry dressing comprising a dry gauze, dry absorbent cotton or any other dry material that may be sterilized by any means known to one of ordinary skill in the art and which does not render the dressing unacceptable for placing over an open wound. The medical dressing as understood by the present disclosure may also comprise a non-adherent dressing that will not adhere to an infected wound or injury, a protective dressing intended to prevent further injury or infection to the infected part of the body, and a wet dressing wherein the dressing is wetted before application to the infected site. The term "medical dressing" may further include an oil-based support such as vitamin E in which an antimicrobial composition according to the present disclosure is dissolved. The oil-base such as, for example, vitamin E can form a barrier to further microbial infection and will leach an antimicrobial composition into the damaged tissue.

In certain instances, the methods, devices, and systems of the disclosure may be used to disinfect/sterilize or maintain a given product essentially 'microbe-free'. Accordingly, a target site may also be an object such as, for example, a medical device (e.g., a catheter or a stent), an artificial prosthetic device (e.g., an artificial joint).

Biofilms on indwelling medical devices can contain populations of gram-positive or gram-negative bacteria or fungi. Gram positive organisms encountered in medical device biofilms are *E. faecalis*, *S. aureus*, *S. epidermidis*, and *S. viridans*. Gram-negative bacteria encountered are *E. coli*, *K. pneumoniae*, *Proteus mirabilis*, and *P. aeruginosa*. These bacteria can are generally derived from the skin of patients or healthcare workers, tap water to which entry ports are exposed, or other sources in the environment such as the patients own stool.

Bacterial biofilms grow when microorganisms irreversibly adhere to a wet surface (such as the internal lumen of a catheter) and produce extracellular polymers that assist adhesion and provide a structural matrix for the colony. The surface that biofilms form on may be inert, nonliving material or living tissue. Microorganisms in a biofilm, behave differently from planktonic (freely suspended) bacteria regarding growth rates and ability to resist antimicrobial treatments, and consequently pose a major medical and public health problem. The present disclosure can inhibit planktonic bacteria from attaching to the surface of a medical device and hence prevent formation of a microbial biofilm.

There are a number of variables that aid in the establishment of whether a contaminated indwelling medical device will develop a biofilm. One factor is that the bacteria or fungus adhere to the exposed surfaces of the device if the exposure time is long enough, and consequently the bacteria or fungus become irreversibly attached. As an example of the problem, urinary catheters (tubular latex or silicone devices), when inserted readily obtain biofilms on the inner or outer surfaces of the catheter. The organisms commonly contaminating these devices and developing biofilms are *S. epidermidis, E. faecalis, E. coli, P. mirabilis, P. aeruginosa, K. pneumoniae*, and other gram-negative organisms. The longer the urinary catheter remains in place, the greater the tendency of these organisms to develop biofilms and result in urinary tract infections, a large medical problem.

The prior art has suggested a number of ways to prevent the occurrence of biofilms in catheters. The conventional methods include using meticulous aseptic technique during implantation, topical antibiotics at the insertion site, minimizing the duration of catheterization, making use of an in-line filter for intravenous fluids, creating mechanical barriers to prevent influx of organisms by attaching the catheter to a surgically implanted cuff, and attempting to coating the inner lumen of the catheter with an antimicrobial agent. However, none of the prior art methods works as effectively as desired.

The methods, systems, and apparatus according to the present disclosure thus, can be used with in-dwelling medical devices such as for example central venous catheters and needleless connectors, endotracheal tubes, peritoneal dialysis catheters, tympanostomy tubes, urinary catheters, and stents, tec. to prevent/mitigate biofilm formation or reduce other biological contaminants as described herein for such devices. Other such medical devices can include, but are not limited to, an IV catheter, a central venous line, an arterial catheter, a peripheral catheter, a dialysis catheter, an external fixator pin, peritoneal dialysis catheter, an epidural catheter, a chest tube, and/or a gastronomy feeding tube Embodiments of the disclosure may also be used to treat biochemical or chemical materials which are infected or may become infected with a biological contaminant (e.g., biochemical or pharmaceutical solution). Most of the methods in the art used to produce preparations to be used in mammals (e.g., immunoglobulin preparations) may result in contamination of the product by pathogens (i.e., biological contaminants). For example, monoclonal immunoglobulin preparations are made in one of three general fashions. The first involves production in a cell culture system, the second uses an animal as a temporary bioreactor for monoclonal immunoglobulin production, and the third involves inserting the gene for a desired monoclonal immunoglobulin into an animal in such a manner as to induce continuous production of the monoclonal immunoglobulin into a fluid or tissue of the animal so that it can be continuously harvested (transgenic production). In the context of the first method, the cells producing the monoclonal immunoglobulin may harbor undetected viruses that can be produced in the culture system. Both of the remaining methods involve the use of an animal to either serve as a host for the monoclonal immunoglobulin-producing cells or as a bioreactor to manufacture the monoclonal immunoglobulin product itself. Obviously, these products face the risk of contamination by pathogens infecting or harbored by the host animal. Such pathogens include, viruses, bacteria, yeasts, molds, mycoplasmas, and parasites, among others. Consequently, it is of importance that any biologically active contaminant in the monoclonal immunoglobulin product be inactivated before the product is used. This is especially important when the product is to be administered directly to a patient. This is also critical for various monoclonal immunoglobulin products which are prepared in media which contain various types of plasma and which may be subject to mycoplasma or other viral contaminants.

Among the viruses of concern for both human and animal-derived biologics, the smallest viruses of concern belong to the family of Parvoviruses and the slightly larger protein-coated Hepatitis virus. In humans, the Parvovirus B19, and Hepatitis A, as well as larger and less hardy viruses such as HIV, CMV, Hepatitis B and C and others, are the agents of concern. In porcine-derived products and tissues, the smallest corresponding virus is Porcine Parvovirus.

The interaction between the target site being treated and the energy imparted is defined by a number of parameters including: the wavelength(s); the chemical and physical properties of the target site; the power density or irradiance of beam; whether a continuous wave (CW) or pulsed irradiation is being used; the laser beam spot size; the exposure time, energy density, and any change in the physical properties of the target site as a result of laser irradiation with any of these parameters. In addition, the physical properties (e.g., absorption and scattering coefficients, scattering anisotropy, thermal conductivity, heat capacity, and mechanical strength) of the target site may also affect the overall effects and outcomes.

The term "NIMELS dosimetery" denotes the power density ($W/cm^2$) and the energy density ($J/cm^2$) (where 1 Watt=1 Joule per second) values at which a subject wavelength according to the disclosure is capable of reducing the level of a biological contaminant in a target site without intolerable risks and/or intolerable side effects on a biological moiety (e.g., a mammalian cell, tissue, or organ) other than the biological contaminant.

As show in FIG. 1 (reproduced in part from Boulnois, Lasers Med. Sci. 1:47-66 (1986) the entire teachings of which are incorporated herein by reference), at low power densities (also referred to as irradiances) and/or energies, the laser-tissue interactions can be described as purely optical (photochemical), whereas at higher power densities photo-thermal interactions ensue. In certain embodiments exemplified hereinafter, NIMELS dosimetry parameters lie between known photochemical and photo-thermal parameters (see, FIG. 1), in an area traditionally used for photodynamic therapy in conjunction with exogenous drugs, dyes at large, and/or chromophores.

As shown in FIG. 1 depending on the interaction, the energy density—also expressible as fluence, or the product (or integral) of particle or radiation flux and time—for medical laser applications in the art typically varies between 1 $J/cm^2$ and 10,000 $J/cm^2$ (five orders of magnitude), whereas the power density (irradiance) varies from $1\times10^{-3}$ $W/cm^2$ to over $10^{12}$ $W/cm^2$ (15 orders of magnitude). Upon taking the reciprocal correlation between the power density and the irradiation exposure time, it can be observed that approximately the same energy density is required for any intended specific laser-tissue interaction. As a result, laser exposure duration (irradiation time) is the primary parameter that determines the nature and safety of laser-tissue interactions. For example, if one were mathematically looking for a thermal vaporization of tissue in vivo (non-ablative) as the laser-tissue interaction of choice for a particular therapy, (based on Boulnois 1986), it can be seen that to produce an energy density of 1000 J/cm$^2$ (within the thermal-vaporization shaded area of FIG. 1) one could use any of the following dosimetry parameters:

TABLE I

Example of Values Derived on the Basis of the Boulnois Table

| POWER DENSITY | TIME | ENERGY DENSITY |
|---|---|---|
| 1 × 10$^5$ W/cm$^2$ | 0.01 sec. | 1000 J/cm$^2$ |
| 1 × 10$^4$ W/cm$^2$ | 0.10 sec. | 1000 J/cm$^2$ |
| 1 × 10$^3$ W/cm$^2$ | 1.00 sec. | 1000 J/cm$^2$ |

This progression describes a suitable method/technique or basic algorithm to be used for a NIMELS interaction against a biological contaminant in a tissue. In other words, this mathematical relation is a reciprocal correlation to achieve a laser-tissue interaction phenomena. This logic is used as a basis for dosimetry calculations for the observed (through experimentation) antimicrobial phenomenon imparted by NIMELS energies with insertion of NIMELS experimental data in the energy density and time and power parameters.

On the basis of the particular interactions at the target site being irradiated (such as the chemical and physical properties of the target site; whether continuous wave (CW) or pulsed irradiation is being used; the laser beam spot size; and any change in the physical properties of the target site—e.g., absorption and scattering coefficients, scattering anisotropy, thermal conductivity, heat capacity, and mechanical strength—, as a result of laser irradiation with any of these parameters), a practitioner is able to adjust the power density and time to obtain the desired energy density.

The examples provided herein show such relationships in the context of both in vitro and in vivo treatments. Hence, in the context of the treatment of onychomycosis, for spot sizes having a diameter of 1-4 cm, power density values were varied from about 0.5 W/cm$^2$ and 5 W/cm$^2$ to stay within safe and non-damaging/minimally damaging thermal laser-tissue interactions well below the level of "denaturization" and "tissue overheating". Other suitable spot sizes may be used.

With this reciprocal correlation, the threshold energy density needed for a NIMELS interaction with these wavelengths can be maintained independent of the spot-size so long as the desired energies are delivered. In exemplary embodiments, the optical energy is delivered through a uniform geometric distribution to the tissues (e.g., a flat-top, or top-hat progression). With such a technique (logic) in mind, a suitable NIMELS dosimetry sufficient to generate a NIMELS effect can calculated to reach the threshold energy densities required to reduce the level of a biological contaminant but below the level of "denaturization" and "tissue overheating".

NIMELS Dosimetries exemplified herein to target microbes in vivo, were 200 J/cm$^2$-700 J/cm$^2$ for approximately 100 to 700 seconds. These power values do not approach power values associated with photoablative or photothermal (laser/tissue) interactions.

Figure 12A:
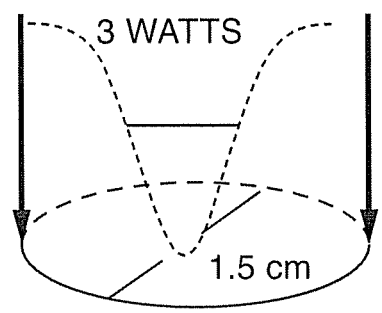
FIGS. 12 *a* and *c* are schematic representation showing the illumination pattern of a 1.5 cm irradiation spot with an incident Gaussian beam pattern of the area of 1.77 cm$^2$.
FIGS. 12*b* and 12*d* show by contrast, the uniform energy distribution ("Top-hat" pattern) used in certain embodiments of the disclosure, with the NIMELS laser system in vivo and in vitro.
Figure 12B:
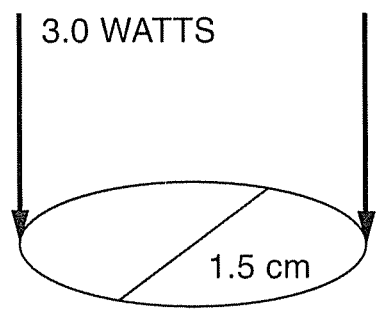
Figure 12C:
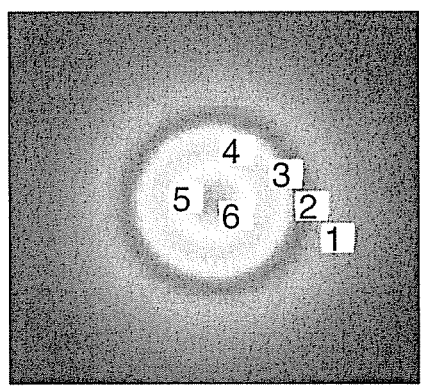

The intensity distribution of a collimated laser beam is given by the power density of the beam, and is defined as the ratio of laser output power to the area of the circle in (cm$^2$). As illustrated in FIGS. 12A and 12C, the illumination pattern of a 1.5 cm irradiation spot with an incident Gaussian beam pattern of the area of 1.77 cm$^2$ may produce at least six different power density values within the 1.77 cm$^2$ irradiation area.

Figure 12D:
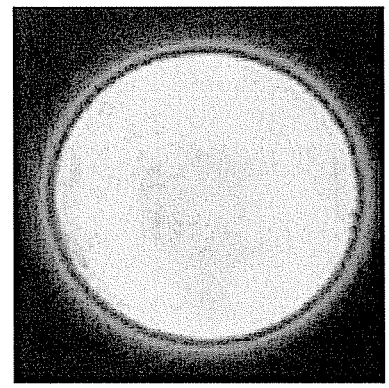

These varying power densities increase in intensity (or concentration of power) over the surface area of the spot from 1 (on the outer periphery) to 6 at the center point. In certain embodiments of the disclosure, a beam pattern is provided which overcomes this inherent error associated with traditional laser beam emissions. FIGS. 12B and 12D show a uniform energy distribution (the "top-hat" pattern as mentioned infra) used in certain embodiments of the disclosure to obtain more consistent power energy values in the irradiation area.

As shown in FIGS. 12B and 12D, in exemplary embodiments, a NIMELS laser system can correct for this error by illuminating in a uniform pattern (top-hat, or a 2π angular step intensity distribution) over an extended area, to insure that there are no or minimal "hot-spots" or "cold spots" in the three dimensional distribution pattern of energy that could negatively interfere with treatment by burning the tissue in the middle of the spot or having a sub-therapeutic energy density on the periphery. Other embodiments may utilize substantially top-hat, e.g., trapezoidal, Gaussian, or other suitable intensity distributions.

In the alternative, NIMELS parameters may be calculated as a function of treatment time (Tn) as follows: Tn=Energy Density/Power Density.

In certain (see e.g., the in vitro experiments exemplified herein) embodiments Tn is of from about 50 to about 300 seconds; in other embodiments, Tn is from about 75 to about 200 seconds; in yet other embodiments, Tn is from about 100 to about 150 seconds. In other in vivo embodiments Tn is from about 100 to about 450 seconds.

Utilizing the above relationships and desired optical intensity distributions, e.g., flat-top illumination geometries as described herein, a series of in vivo energy parameters has been experimentally proven as effective for NIMELS microbial decontamination therapy in vivo. These are shown below for a fixed laser output power of 3 Watts of laser energy for a NIMELS treatment. A key parameter for a given target site has thus been shown to be the energy density required for NIMELS therapy at a variety of different spot sizes and power densities.

Hence, "NIMELS dosimetery" encompasses ranges of power density and/or energy density from a first threshold point at which a subject wavelength according to the disclosure is capable of optically reducing the level of a biological contaminant in a target site to a second end-point immediately before those values at which an intolerable adverse risk or effect is detected (e.g., thermal damage such as, for example, poration) on a biological moiety. One of skill in the art will appreciate that under certain circumstances certain adverse effects and/or risks on a target site (e.g., a mammalian cell, tissues, or organ) may be tolerated in view of the inherent benefits accruing from the methods of the disclosure. Accordingly, the end point contemplated are those at which the adverse effects are considerable and thus, undesired (e.g., cell death, protein denaturation, DNA damage, morbidity, or mortality).

In certain embodiments, e.g., for in vivo applications, the power density range contemplated herein is from about 0.25 to about 40 W/cm$^2$. In other embodiments, the power density range is from about 0.5 W/cm$^2$ to about 25 W/cm$^2$.

In further embodiments, power density ranges can encompass values from about 0.5 W/cm$^2$ to about 10 W/cm$^2$. Power densities exemplified herein are from about 0.5 W/cm$^2$ to about 5 W/cm$^2$. Power densities in vivo from 1.5-2.5 W/cm$^2$ have been shown to be effective for various bacteria.

Empirical data appears to indicate that higher power density values are generally used when targeting a biological contaminant in an in vitro setting (e.g., plates) rather than in vivo (e.g., toe nail).

In certain embodiments (see in vitro examples), the energy density range contemplated herein is greater than 50 J/cm$^2$ but less than about 25,000 J/cm$^2$. In other embodiments, the energy density range is from about 750 J/cm$^2$ to about 7,000 J/cm$^2$. In yet other embodiments, the energy density range is from about 1,500 J/cm$^2$ to about 6,000 J/cm$^2$ depending on whether the biological contaminant is to be targeted in an in vitro setting (e.g., plates) or in vivo (e.g., toe nail or surrounding a medical device).

In certain embodiments (see in vivo examples), the energy density is from about 100 J/cm$^2$ to about 500 J/cm$^2$. In yet other in vivo embodiments, the energy density is from about 175 J/cm$^2$ to about 300 J/cm$^2$. In yet other embodiments, the energy density is from about energy density from about 200 J/cm$^2$ to about 250 J/cm$^2$. In some embodiments, the energy density is from about 300 J/cm$^2$ to about 700 J/cm$^2$. In some other embodiments, the energy density is from about 300 J/cm$^2$ to about 500 J/cm$^2$. In yet others, the energy density is from about 300 J/cm$^2$ to about 450 J/cm$^2$.

Power densities empirically tested for various in vitro treatment of microbial species were from about 1 W/cm$^2$ to about 20 W/cm$^2$.

One of skill in the art will appreciate that the identification of particularly suitable NIMELS dosimetry values within the power density and energy density ranges contemplated herein for a given circumstance may be empirically done via routine experimentation and even by mere trial and error as it is currently done in several presently-available laser uses. Practitioners (e.g., dentists) using near infrared energies in conjunction with periodontal treatment routinely adjust power density and energy density based on the exigencies associated with each given patient (e.g., adjust the parameters as a function of tissue color, tissue architecture, and depth of pathogen invasion). As an example, laser treatment of a periodontal infection in a light-colored tissue (e.g., a melanine deficient patient) will have greater thermal safety parameters than darker tissue, because the darker tissue will absorb near-infrared energy more efficiently, and hence transform these near-infrared energies to heat in the tissues faster. Hence the obvious need for the ability of a practitioner to identify multiple different NIMELS dosimetry values for different therapy protocols.

Any suitable materials (e.g., laser active media, resonator configuration, etc.) and/or methods known to those of skill can be utilized in carrying out the present disclosure. Certain exemplary materials, methods, and configurations are described. Materials, reagents and the like to which reference is made in the following description and examples are obtainable from commercial sources, unless otherwise noted.

Figure 2:
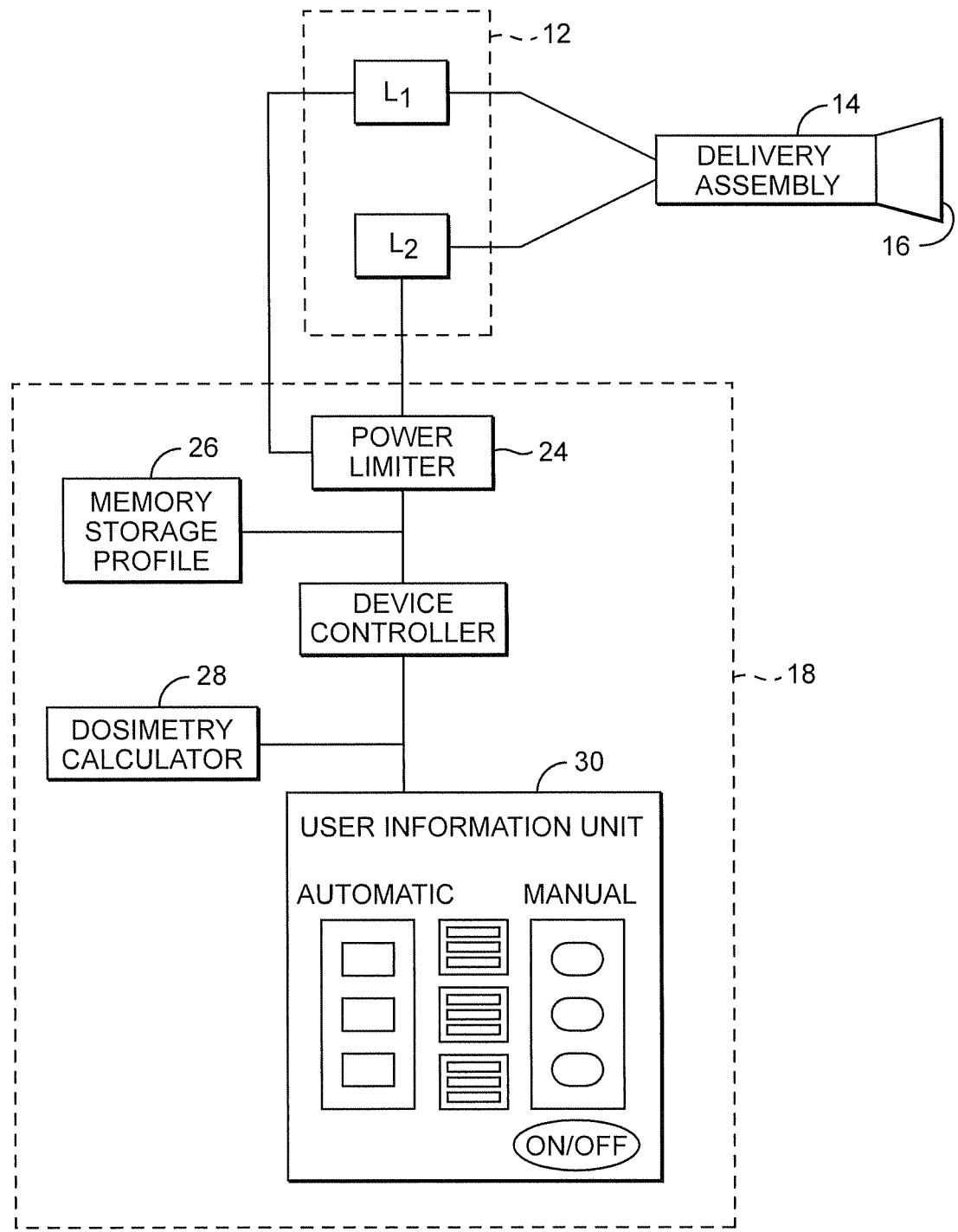
FIG. 2 illustrates a schematic diagram of a system according to one embodiment of the present disclosure.

In a further aspect, the present disclosure provides a therapeutic radiation system (i.e., the NIMELS system). FIG. 2 illustrates a schematic diagram of a therapeutic radiation treatment device according one embodiment of the present disclosure. The therapeutic system 10 includes an optical radiation generation device 12, a delivery assembly 14, an application assembly (or region) 16, and a controller 18. According one aspect of the present disclosure, the optical radiation generation device (source) includes one or more suitable lasers, L1 and L2. A suitable laser may be selected based on a degree of coherence In exemplary embodiments, a therapeutic system can include at least one diode laser configured and arranged to produce an output in the near infrared region. Suitable diode lasers can include a semiconductor materials selected from among $In_xGa_{1-x}As$, $GaAs_{1-x}P_x$, $Al_xGa_{1-x}As$, and $(Al_xGa_{1-x})_yIn_{1-y}As$, for producing radiation in desired wavelength ranges, e.g., 850 nm-900 nm and 905 nm-945 nm (where within each semiconductor alloy, x and y indicate fractions of 1). Suitable diode laser configurations can include cleave-coupled, distributed feedback, distributed Bragg reflector, vertical cavity surface emitting lasers (VCSELS), etc.

With continued reference to FIG. 2, in certain embodiments the delivery assembly 14 can generate a "flat-top" energy profiles for uniform distribution of energy over large areas. As noted, the optical radiation generation device 12 can include one or more lasers, e.g., laser oscillators L1 and L2. In exemplary embodiments, one laser oscillator can be configured to emit optical radiation in a first wavelength range of 850 nm to 900 nm, and the other laser oscillator can be configured to emit radiation in a second wavelength range of 905 nm to 945 nm. In certain embodiments, one laser oscillator is configured to emit radiation in a first wavelength range of 865 nm to 875 nm, and the other laser oscillator 28 is configured to emit radiation in a second wavelength range of 925 nm to 935 nm. The geometry or configuration of the individual laser oscillators may be selected as desired, and the selection may be based on the intensity distributions produced by a particular oscillator geometry/configuration.

With continued reference to FIG. 2, in certain embodiments, the delivery assembly 14 includes an elongated flexible optical fiber adapted for delivery of the dual wavelength radiation from the oscillators 26 and 28 to the application region 16. See also, FIGS. 16 and 17. The delivery assembly 14 may have different formats (e.g., including safety features to prevent thermal damage) based on the application requirements. For example, in one form, the delivery assembly 14 may be constructed with a minimized size and with a shape for inserting into a patient's body.

In alternate forms, the delivery assembly 14 may be constructed with a conical shape for emitting radiation in a diverging-conical manner to apply the radiation to a relatively large area. Hollow waveguides may be used for the delivery assembly 14 in certain embodiments. Other size and shapes of the delivery assembly 14 may also be employed based on the requirements of the application site. In exemplary embodiments, the delivery assembly 14 can be configured for free space or free beam application of the optical radiation, e.g., making use of available transmission through tissue at NIMELS wavelengths described herein. For example, at 930 nm (and to a similar degree, 870 nm), the applied optical radiation can penetrate patient tissue by up to 1 cm or more. Such embodiments may be particularly well suited for use with in vivo medical devices as described below.

In an exemplary embodiment, the controller 18 includes a power limiter 24 connected to the laser oscillators L1 and L2 for controlling the dosage of the radiation transmitted through the application assembly/region 16, such that the time integral of the power density of the transmitted radiation per unit area is below a predetermined threshold, which is set up to prevent damages to the healthy tissue at the application site. The controller 18 may further include a memory 26 for storing treatment information of patients. The stored information of a particular patient may include, but not limited to, dosage of radiation, (for example, including which wavelength, power density, treatment time, skin pigmentation parameters, etc.) and application site information (for example, including type of treatment site (lesion, cancer, etc.), size, depth, etc.).

In an exemplary embodiment, the memory 26 may also be used to store information of different types of diseases and the treatment profile, for example, the pattern of the radiation and the dosage of the radiation, associated with a particular type of disease. The controller 18 may further include a dosimetry calculator 28 to calculate the dosage needed for a particular patient based on the application type and other application site information input into the controller by a physician. In one form, the controller 18 further includes an imaging system for imaging the application site. The imaging system gathers application site information based on the images of the application site and transfers the gathered information to the dosimetry calculator 28 for dosage calculation. A physician also can manually calculate and input information gathered from the images to the controller 18.

As shown in FIG. 2, the controller may further include a control panel 30 through which, a physician can control the therapeutic system manually. The therapeutic system 10 also can be controlled by a computer, which has a control platform, for example, a WINDOWS™ based platform. The parameters such as pulse intensity, pulse width, pulse repetition rate of the optical radiation can be controlled through both the computer and the control panel 30.

Figure 3A:
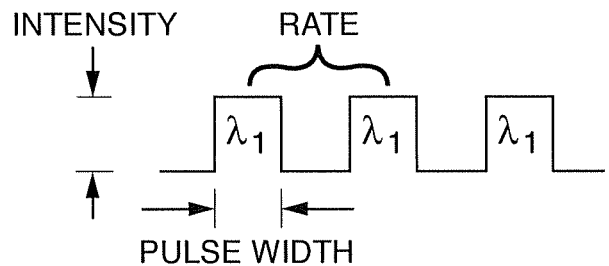
FIGS. 3a-3d illustrate different patterns of optical radiation generated by the therapeutic system of the disclosure of FIG. 2.
Figure 3B:
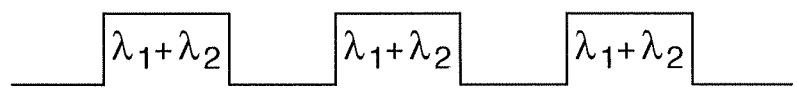
Figure 3C:
Figure 3D:
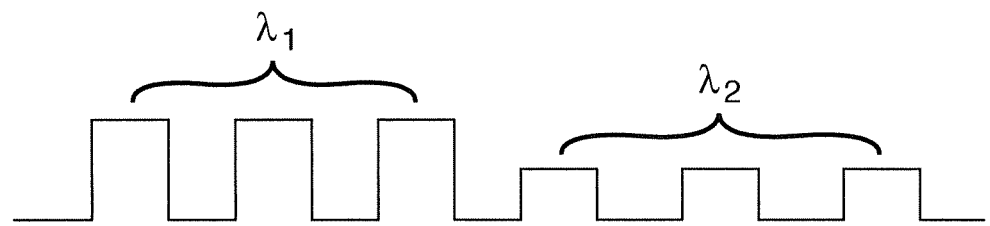

FIGS. 3a-3d show different patterns of the optical radiation that can be delivered from the therapeutic system to the application site. The optical radiation can be delivered in one wavelength range only, for example, in the first wavelength range of 850 nm to 900 nm, or in the range of 865 nm to 875 nm, or in the second wavelength range of 905 nm to 945 nm, or in the range of 925 nm to 935 nm, as shown in FIG. 3a. The radiation in the first wavelength range and the radiation in the second wavelength range also can be multiplexed by a multiplex system installed in the optical radiation generation device 12 and delivered to the application site in a multiplexed form, as shown in FIG. 3b. In an alternative form, the radiation in the first wavelength range and the radiation in the second wavelength range can be applied to the application site simultaneously without passing through a multiplex system. FIG. 3c shows that the optical radiation can be delivered in an intermission-alternating manner, for example, a first pulse in the first wavelength range, a second pulse in the second wavelength range, a third pulse in the first wavelength range again, and a fourth pulse in the second wavelength range again, and so on. The interval can be CW (Continuous Wave), one pulse as shown in FIG. 3c, or two or more pulses (not shown). FIG. 3d shows another pattern in which the application site is first treated by radiation in one of the two wavelength ranges, for example, the first wavelength range, and then treated by radiation in the other wavelength range. The treatment pattern can be determined by the physician based on the type, and other information of the application site.

The following examples are intended to further illustrate certain exemplary embodiments of the disclosure, and are not intended to limit the scope of the disclosure.

EXAMPLE I

NIMELS Dosimetry Calculations

As discussed in more details supra NIMELS parameters include the average single or additive output power of the laser diodes, and the wavelengths (870 nm and 930 nm) of the diodes. This information, combined with the area of the laser beam or beams (cm$^2$) at the target site, provide the initial set of information which may be used to calculate effective and safe irradiation protocols according to the disclosure.

The power density of a given laser measures the potential effect of NIMELS at the target site. Power density is a function of any given laser output power and beam area, and may be calculated with the following equations:

For a single wavelength:

$$\text{Power Density (W/cm}^2\text{)} = \frac{\text{Laser Output Power}}{\text{Beam Diameter (cm}^2\text{)}} \quad 1)$$

For dual wavelength treatments:

$$\text{Power Density (W/cm}^2\text{)} = \quad 2)$$

$$\frac{\text{Laser (1) Output Power}}{\text{Beam Diameter (cm}^2\text{)}} + \frac{\text{Laser (2) Output Power}}{\text{Beam Diameter (cm}^2\text{)}}$$

Beam area can be calculated by either:

$$\text{Beam Area (cm}^2\text{)} = \text{Diameter (cm)}^2 * 0.7854 \text{ or Beam Area (cm}^2\text{)} = \text{Pi} * \text{Radius (cm)}^2 \quad 3)$$

The total photonic energy delivered into the tissue by one NIMELS laser diode system operating at a particular output power over a certain period is measured in Joules, and is calculated as follows:

$$\text{Total Energy (Joules)} = \text{Laser Output Power (Watts)} * \text{Time (Secs.)} \quad 4)$$

The total photonic energy delivered into the tissue by both NIMELS laser diodes systems (both wavelengths) at the same time, at particular output powers over a certain period, is measured in Joules, and is calculated as follows:

$$\text{Total Energy (Joules)} = \quad 5)$$

$$[\text{Laser}(1) \text{ Output Power (Watts)} * \text{Time (Secs)}] +$$

$$[\text{Laser}(2) \text{ Output Power (Watts)} * \text{Time (Secs)}]$$

In practice, it is useful (but not necessary) to know the distribution and allocation of the total energy over the irradiation treatment area, in order to correctly measure dosage for maximal NIMELS beneficial response. Total energy distribution may be measured as energy density (Joules/cm$^2$). As discussed infra, for a given wavelength of light, energy density is the most important factor in determining the tissue reaction. Energy density for one NIMELS wavelength may be derived as follows:

$$\text{Energy Density (Joules/cm}^2\text{)} = \quad 6)$$

$$\frac{\text{Laser Output power (Watts)} * \text{Time (secs)}}{\text{Beam Area (cm}^2\text{)}}$$

$$\text{Energy Density (Joule/cm}^2\text{)} = \text{Power Density (W/cm}^2\text{)} * \text{Time (secs)} \quad 7)$$

When two NIMELS wavelengths are being used, the energy density may be derived as follows:

$$\text{Energy Density (Joules/cm}^2) = \quad\quad\quad 8)$$
$$\frac{\text{Laser (1) Output power (Watts)} * \text{Time (secs)}}{\text{Beam Area (cm}^2)} +$$
$$\frac{\text{Laser (2) Output power (Watts)} * \text{Time (secs)}}{\text{Beam Area (cm}^2)}$$

or, $$\text{Energy Density (Joule/cm}^2) = \quad\quad\quad 9)$$
$$\text{Power Density (1) (W/cm}^2) * \text{Time (secs)} +$$
$$\text{Power Density (2) (W/cm}^2) * \text{Time (secs)}$$

To calculate the treatment time for a particular dosage, a user may use either the energy density (J/cm$^2$) or energy (J), as well as the output power (W), and beam area (cm$^2$) using either one of the following equations:

$$\text{Treatment Time (seconds)} = \frac{\text{Energy Density (Joules/cm}^2)}{\text{Output power Density (W/cm}^2)} \quad 10)$$

$$\text{Treatment Time (seconds)} = \frac{\text{Energy (Joules)}}{\text{Laser Output Power (Watts)}} \quad 11)$$

Because dosimetry calculations such as those exemplified in this Example can become burdensome, the therapeutic system may also include a computer database storing all researched treatment possibilities and dosimetries. The computer (a dosimetry and parameter calculator) in the controller is preprogrammed with algorithms based on the above-described formulas, so that any operator can easily retrieve the data and parameters on the screen, and input additional necessary data (such as: spot size, total energy desired, time and pulse width of each wavelength, tissue being irradiated, bacteria being irradiated) along with any other necessary information, so that any and all algorithms and calculations necessary for favorable treatment outcomes can be generated by the dosimetry and parameter calculator and hence run the laser.

The following examples describe selected experiments showing the ability of the NIMELS approach to impact upon the viability of various commonly found microorganisms at the wavelengths as described herein. The microorganisms exemplified include *E. coli* K-12, multi-drug resistant *E. coli*, *Staphylococcus aureus*, Methicillin-resistant *S. aureus*, *Candida albicans*, and *Trichophyton rubrum*.

In summary, when the bacterial cultures were exposed to the NIMELS laser, the bacterial kill rate (as measured by counting Colony Forming Units or CFU on post-treatment culture plates) ranged from 93.7% (multi-drug resistant *E. coli*) to 100% (all other bacteria and fungi).

EXAMPLE II

Bacterial Methods: NIMELS Treatment Parameters for In Vitro *E. coli* Targeting

The following parameters illustrate the methods according to the disclosure as applied to *E. coli*, at final temperatures well below those associated in the literature with thermal damage.

A. Experiment Materials and Methods for *E. coli* K-12:
*E. coli* K12 liquid cultures were grown in Luria Bertani (LB) medium (25 g/L). Plates contained 35 mL of LB plate medium (25 g/L LB, 15 g/L, bacteriological agar). Cultures dilutions were performed using phosphate-buffered saline (PBS). All protocols and manipulations were performed using sterile techniques.
B. Growth Kinetics
Drawing from a seed culture, multiple 50 mL LB cultures were inoculated and grown at 37° C. overnight. The next morning, the healthiest culture was chosen and used to inoculate 5% into 50 mL LB at 37° C. and the O.D.$_{600}$ was monitored over time taking measurements every 30 to 45 minutes until the culture was in stationary phase.
C. Master Stock Production
Starting with a culture in log phase (O.D.$_{600}$ approximately 0.75), 10 mL were placed at 4° C. 10 mL of 50% glycerol were added and then this was aliquoted to 20 cryovials and snap frozen in liquid nitrogen. The cryovials were then stored at −80° C.
D. Liquid Cultures
Liquid cultures of *E. coli* K12 were set up as described previously. An aliquot of 100 µL was removed from the subculture and serially diluted to 1:1200 in PBS. This dilution was allowed to incubate at room temperature approximately 2 hours or until no further increase in O.D.$_{600}$ was observed in order to ensure that the cells in the PBS suspension would reach a static state (growth) with no significant doubling and a relatively consistent number of cells could be aliquoted further for testing.

Once it was determined that the K12 dilution was in a static state, 2 mL of this suspension were aliquoted into selected wells of 24-well tissue culture plates for selected NIMELS experiments at given dosimetry parameters. The plates were incubated at room temperature until ready for use (approximately 2 hrs).

Following laser treatments, 100 µl was removed from each well and serially diluted to 1:1000 resulting in a final dilution of 1:12×10$^5$ of initial K12 culture. Aliquots of 3×200 L of each final dilution were spread onto separate plates in triplicate. The plates were then incubated at 37° C. for approximately 16 hours. Manual colony counts were performed and recorded. A digital photograph of each plate was also taken.

Similar cell culture and kinetic protocols were performed for all NIMELS irradiation tests with *S. aureus* and *C. albicans* in vitro tests. Hence, for example, *C. albicans* ATCC 14053 liquid cultures were grown in YM medium (21 g/L, Difco) medium at 37° C. A standardized suspension was aliquoted into selected wells in a 24-well tissue culture plate. Following laser treatments, 100 µL was removed from each well and serially diluted to 1:1000 resulting in a final dilution of 1:5×10$^5$ of initial culture. 3×100 µL of each final dilution were spread onto separate plates. The plates were then incubated at 37° C. for approximately 16-20 hours. Manual colony counts were performed and recorded. A digital photograph of each plate was also taken.

*T. rubrum* ATCC 52022 liquid cultures were grown in peptone-dextrose (PD) medium at 37° C. A standardized suspension was aliquoted into selected wells in a 24-well tissue culture plate. Following laser treatments, 3×100 µL aliquots were removed from each well and spread onto separate plates. The plates were then incubated at 37° C. for approximately 91 hours. Manual colony counts were performed and recorded after 66 hours and 91 hours of incubation. While control wells all grew the organism, 100% of laser-treated wells as described herein had no growth. A digital photograph of each plate was also taken.

Thermal tests performed on PBS solution, starting from room temperature. 10 Watts of NIMELS laser energy is available for use in a 12 minute lasing cycle, before the temperature of the system is raised close to the critical threshold of 44° C.

TABLE II

Time Temperature measurements for In Vitro NIMELS Dosimetries

| NIMEL OUTPUT POWER (W) | BEAM SPOT 1.5 CM DIAMETER OVERLAP AREA (CM$^2$) | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) | TEMPERATURE START | TEMP FINISH |
|---|---|---|---|---|---|---|---|
| Plate 1-N - 3.0 + 3.0 = 6.0 W | 1.76 | 720 | 4320 | 2448 | 3.40 | 20.5° C. | 34.0° C. |
| Plate 2-N - 3.5 + 3.5 = 7.0 W | 1.76 | 720 | 5040 | 2858 | 3.97 | 20.7° C. | 36.5° C. |
| Plate 3-N - 4.0 + 4.0 = 8.0 W | 1.76 | 720 | 5760 | 3268 | 4.54 | 21.0° C. | 38.5° C. |
| Plate 4-N - 4.5 + 4.5 = 9.0 W | 1.76 | 720 | 6480 | 3679 | 5.11 | 2.0° C. | 41.0° C. |
| Plate 5-N - 5.0 + 5.0 = 10. W | 1.76 | 720 | 7200 | 4089 | 5.68 | 21.0° C. | 40.5° C. |
| Plate 6-N - 5.5 + 5.5 = 11 W | 1.76 | 720 | 7920 | 4500 | 6.25 | 21.0° C. | 46.0° C. |
| Plate 7-N - 7.0 + 7.0 = 14.0 W | 1.76 | 360 | 5040 | 2863 | 7.95 | 21.0° C. | 47.0° C. |
| Plate 8-N - 7.5 + 7.5 = 15 W | 1.76 | 360 | 5400 | 3068 | 8.52 | 21.7° C. | 47.2° C. |

EXAMPLE III

Dosimetry Values for NIMELS Laser Wavelength 930 nm for *E. coli* In Vitro Targeting The instant experiment shows that the NIMELS single wavelength λ=930 nm was associated with quantitatable antibacterial efficacy against *E. coli* in vitro within safe thermal parameters for mammalian tissues.

Experimental data in vitro demonstrates that if the threshold of total energy into the system with 930 nm alone of 5400 J and an energy density of 3056 J/cm$^2$ is met in 25% less time, 100% antibacterial efficacy is still achieved.

TABLE III

Sub-thermal NIMELS (λ = 930) Dosimetry for In Vitro *E. coli* Targeting

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) | *E-COLI* KILL PERCENTAGE |
|---|---|---|---|---|---|---|
| 7.0 | 1.5 | 720 | 5040 | 2852 | 3.96 | 40.2% |
| 8.0 | 1.5 | 720 | 5760 | 3259 | 4.53 | 100.0% |
| 10.0 | 1.5 | 540 | 5400 | 3056 | 5.66 | 100.0% |

Experimental data in vitro also demonstrated that treatments using a single energy with λ=930 nm had antibacterial efficacy against the bacterial species *S. aureus* in vitro within safe thermal parameters for mammalian tissues.

It is also believed that if the threshold of total energy into the system of 5400 J and an Energy Density of 3056 J/cm$^2$ is met in 25% less time with *S. aureus* and other bacterial species, that 100% antibacterial efficacy will still be achieved.

TABLE IV

Sub-thermal NIMELS (λ = 930) Dosimetry for In Vitro *S. aureus* Targeting

| OUTPUT POWER (W) | BEAM SPOT (CM) | TIME (SEC) | TOTAL ENERGY JOULES | ENERGY DENSITY (J/CM$^2$) | POWER DENSITY (W/CM$^2$) | *S AUREUS* KILL PERCENTAGE |
|---|---|---|---|---|---|---|
| 7.0 | 1.5 | 720 | 5040 | 2852 | 3.96 | 24.1% |
| 8.0 | 1.5 | 720 | 5760 | 3259 | 4.53 | 100.0% |

Experimental data in vitro also showed that the NIMELS single wavelength of λ=930 μm had anti-fungal efficacy against *C. albicans* in vitro at ranges within safe thermal parameters for mammalian tissues.

It is also believed that if the threshold of total energy into the system of 5400 J and an energy density of 3056 J/cm² is met in 25% less time, that 100% antifungal efficacy will still be achieved. See also FIG. 3.

TABLE V

Sub-thermal NIMELS (λ = 930) Dosimetry for In Vitro *C. albicans* Targeting

| OUTPUT POWER (W) | BEAM SPOT (CM) | TIME (SEC.) | TOTAL ENERGY JOULES | ENERGY DENSITY (J/CM²) | POWER DENSITY (W/CM²) | *CANDIDA ALBICANS* KILL PERCENTAGE |
|---|---|---|---|---|---|---|
| 8.0 | 1.5 | 720 | 5760 | 3259 | 4.53 | 100.0% |
| 9.0 | 1.5 | 720 | 6840 | 3681 | 5.11 | 100.0% |

EXAMPLE IV

Dosimetry Values for NIMELS Laser Wavelength 870 nm In Vitro

Experimental data in vitro also demonstrated that no significant kill was achieved up to a total energy of 7200 J, and energy density of 4074 J/cm² and a power density of 5.66 0 W/cm² with the wavelength of 870 nm alone against *E. coli*.

TABLE VI

*E. coli* Studies-Single wavelength λ = 870 nm

| OUTPUT POWER (W) | BEAM SPOT (CM) | TIME (SEC.) | TOTAL ENERGY JOULES | ENERGY DENSITY (J/CM²) | POWER DENSITY (W/CM²) | CONTROL CFUs | NIMELS CFUs | DIFFERENCE CONTROL − NIMEL | *E COLI* KILL PERCENTAGE |
|---|---|---|---|---|---|---|---|---|---|
| 6.0 | 1.5 | 720 | 4320 | 2445 | 3.40 | 90 | 95 | (5) | −5.6% |
| 7.0 | 1.5 | 720 | 5040 | 2852 | 3.96 | 94 | 94 | 0 | 0.0% |
| 8.0 | 1.5 | 720 | 5760 | 3259 | 4.53 | 93 | 118 | (25) | −26.9% |
| 9.0 | 1.5 | 720 | 6480 | 3667 | 5.09 | 113 | 112 | 1 | 0.9% |
| 10.0 | 1.5 | 720 | 7200 | 4074 | 5.66 | 103 | 111 | (8) | −7.8% |
| 10.0 | 1.5 | 540 | 5400 | 3056 | 5.66 | 120 | 101 | 19 | 15.8% |

Comparable results using radiation having λ=870 nm alone were also observed with *S. aureus*.

EXAMPLE V

NIMELS Unique Alternating Synergistic Effect Between 870 nm and 930 nm Optical Energies Experimental data in vitro also demonstrated that there is an additive effect between the two NIMELS wavelengths (λ=870 nm and 930 nm) when they are alternated (870 nm before 930 nm). The presence of the 870 nm NIMELS wavelength as a first irradiance has been found to enhance the effect of the antibacterial efficacy of the second 930 nm NIMELS wavelength irradiance.

Experimental data in vitro demonstrates that this synergistic effect (combining the 870 nm wavelength to the 930 nm wavelength) allows for the 930 nm optical energy to be reduced. As shown hereinafter, the optical energy was reduced to approximately ⅓ of the total energy and energy density required for NIMELS 100% *E. coli* antibacterial efficacy, when the (870 nm before 930 nm) wavelengths are combined in an alternating manner.

Experimental data in vitro also demonstrates that this synergistic mechanism can allow for the 930 nm optical energy (total energy and energy density) to be reduced to approximately ½ of the total energy density necessary for NIMELS 100% *E. coli* antibacterial efficacy if equal amounts of 870 nm optical energy are added to the system before the 930 nm energy at 20% higher power densities.

TABLE VII

*E. coli* data from Alternating NIMELS Wavelengths

| OUTPUT POWER (W) | SPOT (CM) | TIME (SEC.) | TOTAL ENERGY JOULES | ENERGY DENSITY (J/CM$^2$) | POWER DENSITY (W/CM$^2$) | *E. COLI* KILL PERCENTAGE |
|---|---|---|---|---|---|---|
| 8 W/8 W | 1.5 | 540/180 12 min. | 4320/1440 = 5760 | 2445/815 = 3529 | 4.53/4.53 | 100.0% |
| 10 W/10 W | 1.5 | 240/240 8 min. | 2400/2400 = 4800 | 1358/1358 = 2716 | 5.66/5.66 | 100.0% |

This synergistic ability is significant to human tissue safety, as the 930 nm optical energy, heats up a system at a greater rate than the 870 nm optical energy, and it is beneficial to a mammalian system to produce the least amount of heat possible during treatment.

It is also believed that if the NIMELS optical energies (870 nm and 930 nm) are alternated in the above manner with other bacterial species, that the 100% antibacterial effect will be essentially the same.

Experimental data in vitro also demonstrates that there is also an additive effect between the two NIMELS wavelengths (870 nm and 930 nm) when they are alternated (870 nm before 930 nm) while irradiating fungi. The presence of the 870 nm NIMELS wavelength as a first irradiance mathematically enhances the effect of the anti-fungal efficacy of the second 930 nm NIMELS wavelength irradiance.

Experimental data in vitro (see, table infra) demonstrates that this synergistic mechanism can allow for the 930 nm optical energy (total energy and energy density) to be reduced to approximately ½ of the total energy density necessary for NIMELS 100% antifungal efficacy if equal amounts of 870 nm optical energy is added to the system before the 930 nm energy at 20% higher power densities than is required for bacterial species antibacterial efficacy.

rate than the 870 nm optical energy, and it is beneficial to a mammalian system to produce the least amount of heat possible during treatment.

It is also believed that if the NIMELS optical energies (870 nm and 930 nm) are alternated in the above manner with other fungi species, that the 100% anti-fungal effect will be essentially the same.

EXAMPLE VI

NIMELS Unique Simultaneous Synergistic Effect Between $\Lambda$=870 nm and $\Lambda$=930 nm Optical Energies Experimental data in vitro also demonstrates that there is an additive effect between the two NIMELS wavelengths (870 nm and 930 nm) when they are used simultaneously (870 nm combined with 930 nm). The presence of the 870 nm NIMELS wavelength and the 930 nm NIMELS wavelength as a simultaneous irradiance absolutely enhances the effect of the antibacterial efficacy of the NIMELS system.

In vitro experimental data (see, for example, Tables IX and X below) demonstrated that by combining $\lambda$=870 nm and $\lambda$=930 nm (in this example, used simultaneously) effectively reduces the 930 nm optical energy and density by about half

TABLE VIII

*C. albicans* Data from Alternating NIMEL Wavelengths

| OUTPUT POWER (W) | SPOT (CM) | TIME (SEC) | TOTAL ENERGY JOULES | ENERGY DENSITY (J/CM$^2$) | POWER DENSITY (W/CM$^2$) | *CANDIDA ALBICANS* KILL PERCENTAGE |
|---|---|---|---|---|---|---|
| 10 W/ 10 W | 1.5 | 240/240 8 min | 2400/2400 = 4800 | 1358/1358 = 2716 | 5.66/5.66 | 100.0%* |

This synergistic effect is significant to human tissue safety, as the 930 nm optical energy, heats up a system at a greater of the total energy and energy density required when using a single treatment according to the disclosure.

TABLE IX

*E. coli* data from Combined NIMEL Wavelengths

| OUTPUT POWER (W) 870 NM/ 930 NM | BEAM SPOT (CM) | TIME (SEC) | TOTAL ENERGY JOULES | ENERGY DENSITY (J/CM$^2$) | POWER DENSITY (W/CM$^2$) | E-COLI KILL PERCENTAGE |
|---|---|---|---|---|---|---|
| 5 W + 5 W = 10 | 1.5 | 720 | 3600 (×2) = 7200 | 2037 (×2) = 4074 | 5.66 | 100% |

TABLE X

*S. aureus* data from Combined NIMELS Wavelengths

| OUTPUT POWER (W) 870 NM/ 930 NM | BEAM SPOT (CM) | TIME (SEC) | TOTAL ENERGY JOULES | ENERGY DENSITY (J/CM²) | POWER DENSITY (W/CM²) | *S. AUREUS* KILL PERCENTAGE |
|---|---|---|---|---|---|---|
| 5 W + 5 W = 10 W | 1.5 | 720 | 3600 (×2) = 7200 | 2037 (×2) = 4074 | 5.66 | 98.5% |
| 5.5 W + 5.5 = 11 W | 1.5 | 720 | 3960 (×2) = 7920 | 2241 (×2) = 4482 | 6.22 | 100% |

This simultaneous synergistic ability is significant to human tissue safety, as the 930 nm optical energy, heats up a system at a greater rate than the 870 nm optical energy, and it is beneficial to a mammalian system to produce the least amount of heat possible during treatment.

Figure 4:
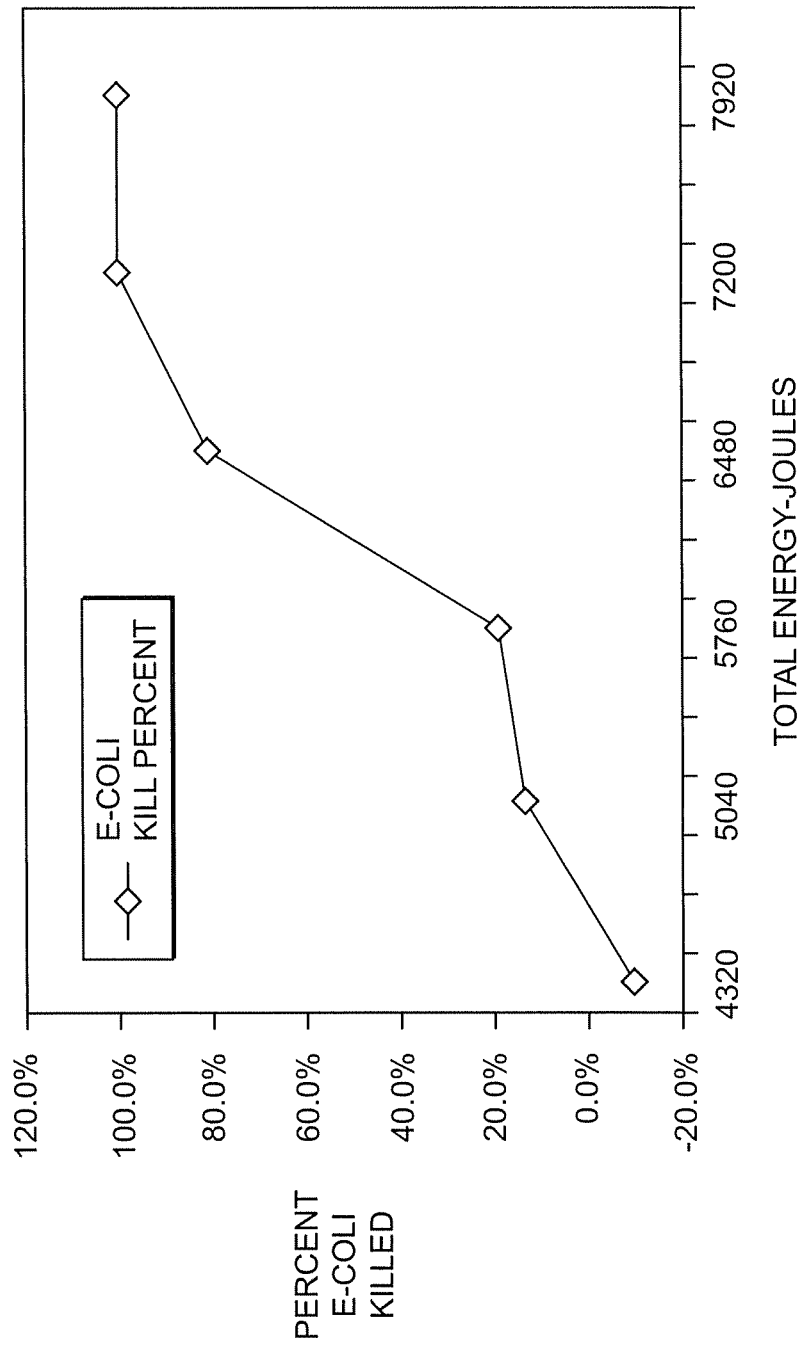
FIG. 4 is a graphic representation of typical in vitro efficacy data (in percent kill) obtained using representative methods, devices and systems of the disclosure to target *E. coli* cells at different total energy values (in Joules).
Figure 5:
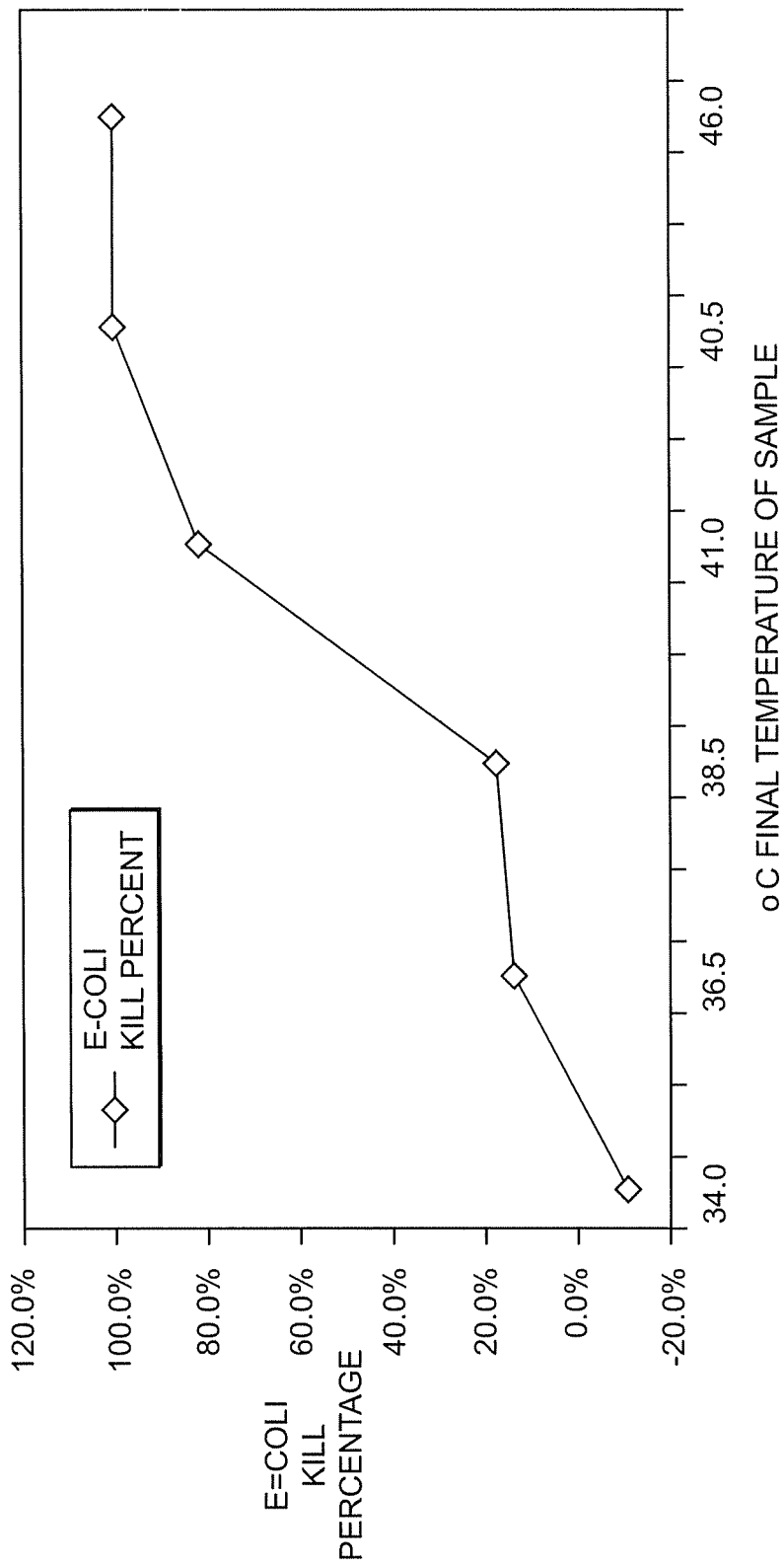
FIG. 5 is a graphic representation of typical final sample temperatures (in ° C.) observed using representative methods and systems of the disclosure to target *E. coli* cells at different total energy values (in Joules).

It is now understood that if the NIMELS optical energies (870 nm and 930 nm) are used simultaneously in the above manner with other bacterial species, that the 100% antibacterial effect will be essentially the same. See FIGS. 4 and 5.

Experimental data in vitro also demonstrates that there is an additive effect between the two NIMELS wavelengths (870 nm and 930 nm) when they are used simultaneously on fungi. The presence of the 870 nm NIMELS wavelength and the 930 nm NIMELS wavelength as a simultaneous irradiance have been found to enhance the effect of the anti-fungal efficacy of the NIMELS system.

Experimental data in vitro (see Table X) demonstrates that this synergistic effect (connecting the 870 nm wavelength to the 930 nm wavelength for simultaneous irradiation) allows for the 930 nm optical energy to be reduced to approximately ½ of the total energy and energy density required for NIMELS 100% *C. albicans* anti-fungal efficacy, when the (870 nm before 930 nm) wavelengths are combined in a simultaneous manner.

TABLE XI

*Candida albicans* from Combined NIMELS Wavelengths

| OUTPUT POWER (W) 870 NM/ 930 NM | BEAM SPOT (CM) | TIME (SEC) | TOTAL ENERGY JOULES | ENERGY DENSITY (J/CM²) | POWER DENSITY (W/CM²) | *C. ALBICANS* KILL PERCENTAGE |
|---|---|---|---|---|---|---|
| 5 W + 5 W = 10 | 1.5 | 720 | 3600 (×2) = 7200 | 2037 (×2) = 4074 | 5.66 | 100% |

Thus NIMELS wavelengths ($\lambda$=870 nm and 930 nm) may be used to achieve antibacterial and anti-fungal efficacy in an alternating mode or simultaneously or in any combination of such modes thereby reducing the exposure at the $\lambda$=930 associated with temperature increases which are preferably minimized.

Experimental data in vitro also demonstrates that when *E. coli* is irradiated alone with a (control) wavelength of $\lambda$=830 nm, at the following parameters (see Table XI), the control 830 nm laser produced zero antibacterial efficacy for 12 minutes irradiation cycles, at identical parameters to the minimum NIMELS dosimetry associated with 100% antibacterial and anti-fungal efficacy with radiation of $\lambda$=930 nm.

TABLE XII

*E. coli* Single Wavelength $\lambda$ = 830 nm

| OUTPUT POWER (W) | BEAM SPOT (CM) | TIME (SEC.) | TOTAL ENERGY JOULES | ENERGY DENSITY (J/CM²) | POWER DENSITY (W/CM²) |
|---|---|---|---|---|---|
| 8.0 | 1.5 | 720 | 5760 | 3259 | 4.53 |
| 9.0 | 1.5 | 720 | 6480 | 3667 | 5.09 |

Experimental data in vitro also demonstrates that when applied at safe thermal dosimetries, there is little additive effect when using radiance of $\lambda$=830 nm in combination with $\lambda$=930 nm. The presence of the 830 nm control wavelength as a first irradiance, is far inferior to the enhancement effect of the 870 nm NIMELS wavelength in producing synergistic antibacterial efficacy with the second 930 nm NIMELS wavelength.

TABLE XIII

E. coli data from Substituted alternating 830 nm control Wavelength

| OUTPUT POWER (W) 830 NM/ 930 NM | BEAM SPOT (CM) | TIME (SEC) | TOTAL ENERGY JOULES | ENERGY DENSITY (J/CM$^2$) | POWER DENSITY (W/CM$^2$) | E. COLI KILL PERCENTAGE |
|---|---|---|---|---|---|---|
| 8 W/8 W | 1.5 | 540/180 12 min | 4320/1440 = 5760 | 2445/815 = 3529 | 4.53/4.53 | 0% |
| 10 W/10 W | 1.5 | 240/240 8 min | 2400/2400 = 4800 | 1358/1358 = 2716 | 5.66/5.66 | 65% |

Experimental data in vitro also demonstrates that when applied at safe thermal dosimetries, there is less additive effect with the 830 nm wavelength, and the NIMELS 930 nm wavelength when they are used simultaneously. In fact, experimental data in vitro demonstrates that 17% less total energy, 17% less energy density, and 17% less power density is required to achieve 100% E. coli antibacterial efficacy when 870 nm is combined simultaneously with 930 nm, vs. the commercially available 830 nm. This again substantially reduces heat and harm to the in vivo system being treated with the NIMELS wavelengths.

TABLE XIV

E. coli data from Substituted Simultaneous 830 nm control Wavelength

| OUTPUT POWER (W) 830 NM/ 930 NM | BEAM SPOT (CM) | TIME (SEC) | TOTAL ENERGY JOULES | ENERGY DENSITY (J/CM$^2$) | POWER DENSITY (W/CM$^2$) | E-COLI KILL PERCENTAGE |
|---|---|---|---|---|---|---|
| 5 W + 5 W = 10 | 1.5 | 720 | 3600 (×2) = 7200 | 2037 (×2) = 4074 | 5.66 | 91% |
| 5.5 W + 5.5 = 11 W | 1.5 | 720 | 3960 (×2) = 7920 | 2250 (×2) = 4500 | 6.25 | 90% |
| 6 W + 6 W = 12 W | 1.5 | 720 | 3960 (×2) f = 8640* | 2454 (×2) = 4909* | 6.81* | 100% |

Amount of Bacteria Killed:

In vitro data also showed that the NIMELS laser system in vitro is effective (within thermal tolerances) against solutions of bacteria containing 2,000,000 (2×10$^6$) Colony Forming Units (CFU's) of E. coli and S. aureus. This is a 2× increase over what is typically seen in a 1 gm sample of infected human ulcer tissue. Brown et al. reported that microbial cells in 75% of the diabetic patients tested were all at least 100,000 CFU/gm, and in 37.5% of the patients, quantities of microbial cells were greater than 1,000,000 (1×10$^6$) CFU (see, Brown et al., Ostomy Wound Management, 401:47, issue 10, (2001) the entire teachings of which are incorporated herein by reference in their entirety).

Figure 6:
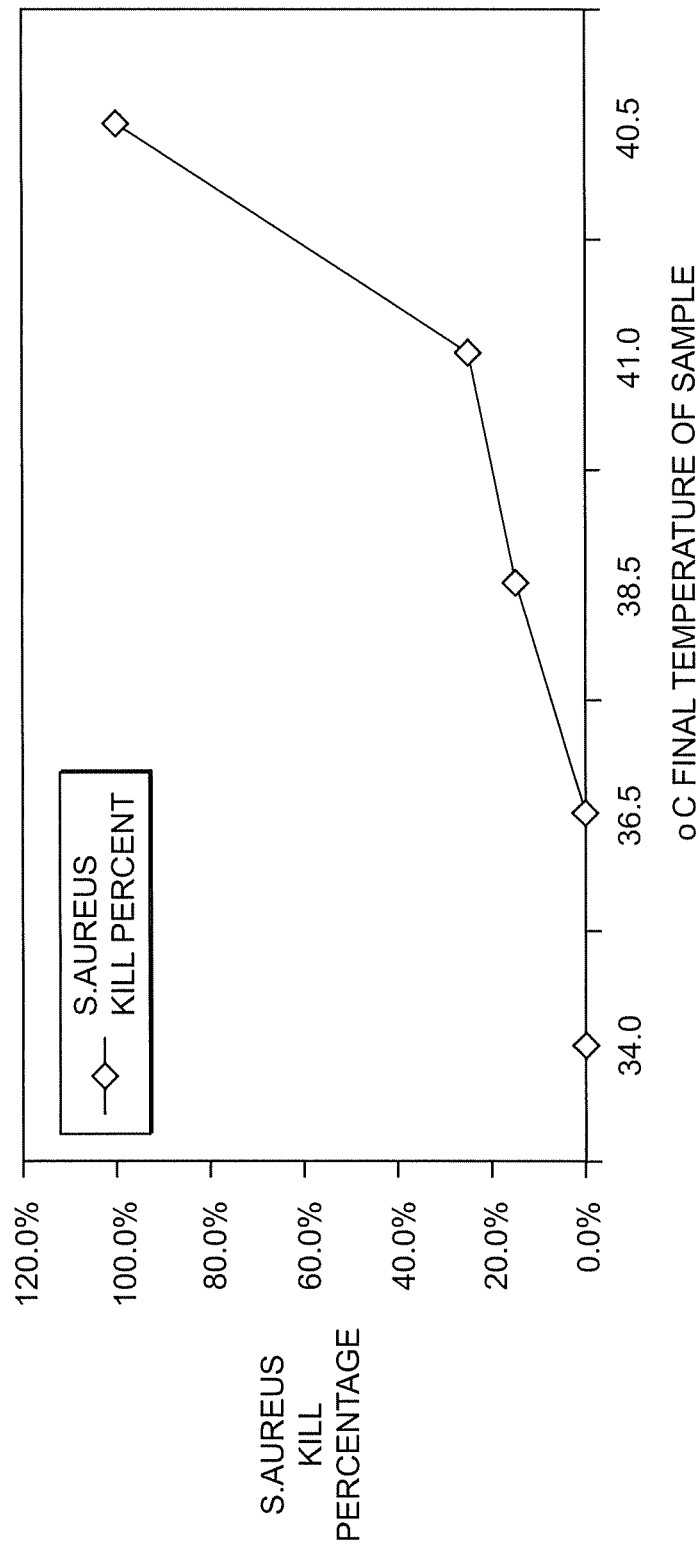
FIG. 6 is a graphic representation of typical final sample temperatures (in ° C.) observed in vitro using representative methods and systems of the disclosure to target *S. aureus* cells at different total energy values (in Joules).
Figure 7:
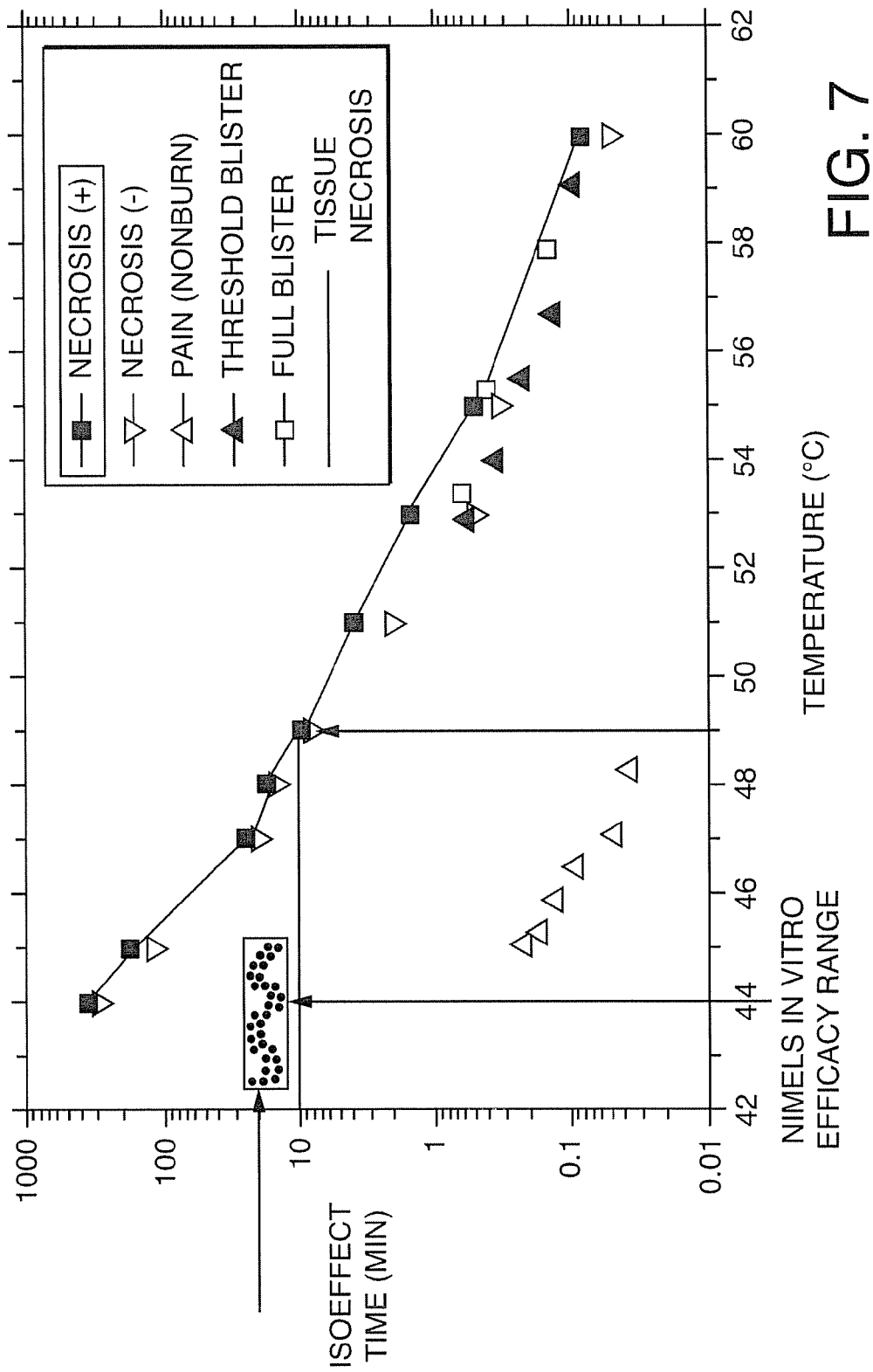
FIG. 7 is a graphic representation showing typical in vitro efficacy data observed using representative methods and systems of the disclosure at thermally tolerable temperatures of the treated target site.

Thermal Parameters:

Experimental data in vitro also demonstrates that the NIMELS laser system can accomplish 100% antibacterial and anti-fungal efficacy within safe thermal tolerances for human tissues. See FIG. 6.

EXAMPLE VII

The Effects of Lower Temperatures on NIMELS

Dewhirst et al., Internat. J. of Hyperthermia, 19(3):267-294 reported the effects of lower temperature on bacteria; the entire teachings of which are incorporated herein by reference in their entirety.

Cooling of Bacterial Species:

Experimental data in vitro also demonstrated that by substantially lowering the starting temperature of bacterial samples to 4° C. for two hours in PBS before lasing cycle, that optical antibacterial efficacy was not achieved at any currently reproducible antibacterial energies with the NIMELS laser system.

The most probable explanation is that the bacterial cells were in "metabolic stasis" and that little or no radical oxygen was produced without active metabolism occurring in the cells. This data indicates that NIMELS may be affecting respiratory centers and cell membranes of the targeted microorganisms.

The postulated mechanism is that the 870 nm energy effects the cytochromes by speeding up oxidative phosphorylation while the 930 nm energy disrupts cell membranes and hence produces singlet oxygen via uncoupling the electron transport system, and not allowing the terminal O$_2$ molecule to be reduced.

EXAMPLE VIII

Trychophyton Rubrum

TABLE XV

NIMELS *T. rubrum* Tests Alternating Wavelengths

| EXP. NO. | OUTPUT POWER (W) 870 NM/ 930 NM | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 1 | 8 W/8 W | 1.5 | 540/180 12 min. | 4320/1440 = 5760 | 2445/815 = 3529 | 4.53/4.53 |
| 2 | 10 W/10 W | 1.5 | 240/240 8 min. | 2400/2400 = 4800 | 1358/1358 = 2716 | 5.66/5.66 |

Experiment No. 1 = Minimal Effect
Experiment No. 2 = 100% Kill in all plates

TABLE XVI

NIMELS *T. rubrum* - Simultaneous Wavelengths

| EX NO. | OUTPUT POWER (W) Λ = 870 NM & Λ = 930 NM | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 3 | 5 + 5 = 10 | 1.5 | 720 12 min. | 3600 (x2) = 7200 | 2037 (x2) = 4074 | 5.66 |
| 4 | 5.5 W + 5.5 W = 11 W | 1.5 | 720 | 3960 (x2) = 7920 | 2250 (x2) = 4500 | 6.25 |
| 5 | 6 W + 6 W = 12 W | 1.5 | 720 | 3960 (x2) = 8640 | 2454 (x2) = 4909 | 6.81 |

Experiments Nos. 3, 4, and 5 = 100% Kill in all plates

TABLE XVII

NIMELS *T. rubrum* - Single Wavelength

| EXP NO λ = 930 | OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 6 | 8.0 | 1.5 | 720 | 5760 | 3259 | 4.53 |
| 7 | 9.0 | 1.5 | 720 | 6840 | 3681 | 5.11 |

Experiments Nos. 6 and 7 = 100% Kill in all plates

TABLE XVIII

Control *T. rubrum* - 830 nm/930 nm Alternating

| EXPERIMENT NO. λ 830 & λ = 930 | OUTPUT POWER (W) | BEAM SPOT (CM) | TIME (MIN.) | TOTAL ENERGY JOULES | ENERGY DENSITY (J/CM$^2$) | POWER DENSITY (W/CM$^2$) |
|---|---|---|---|---|---|---|
| 8 | 8 W/8 W | 1.5 | 540/180 12 min | 4320/1440 = 5760 | 2445/815 = 3529 | 4.53/4.53 |
| 9 | 10 W/10 W | 1.5 | 240/240 8 min | 2400/2400 = 4800 | 1358/1358 = 2716 | 5.66/5.66 |

Experiment No. 8 = No Effect
Experiment No. 9 = 100% Kill

TABLE XIX

In Vitro Targeting of *T. rubrum* using λ = 830 nm and 930 nm

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|
| 5 + 5 = 10 | 1.5 | 720 | 3600 (×2) = 7200 | 2037 (×2) = 4074 | 5.66 |

Treatments as described in the above Table XVIII resulted in 100% kill.

EXAMPLE IX

Onychomycosis Treatment Evaluation

Figure 8:
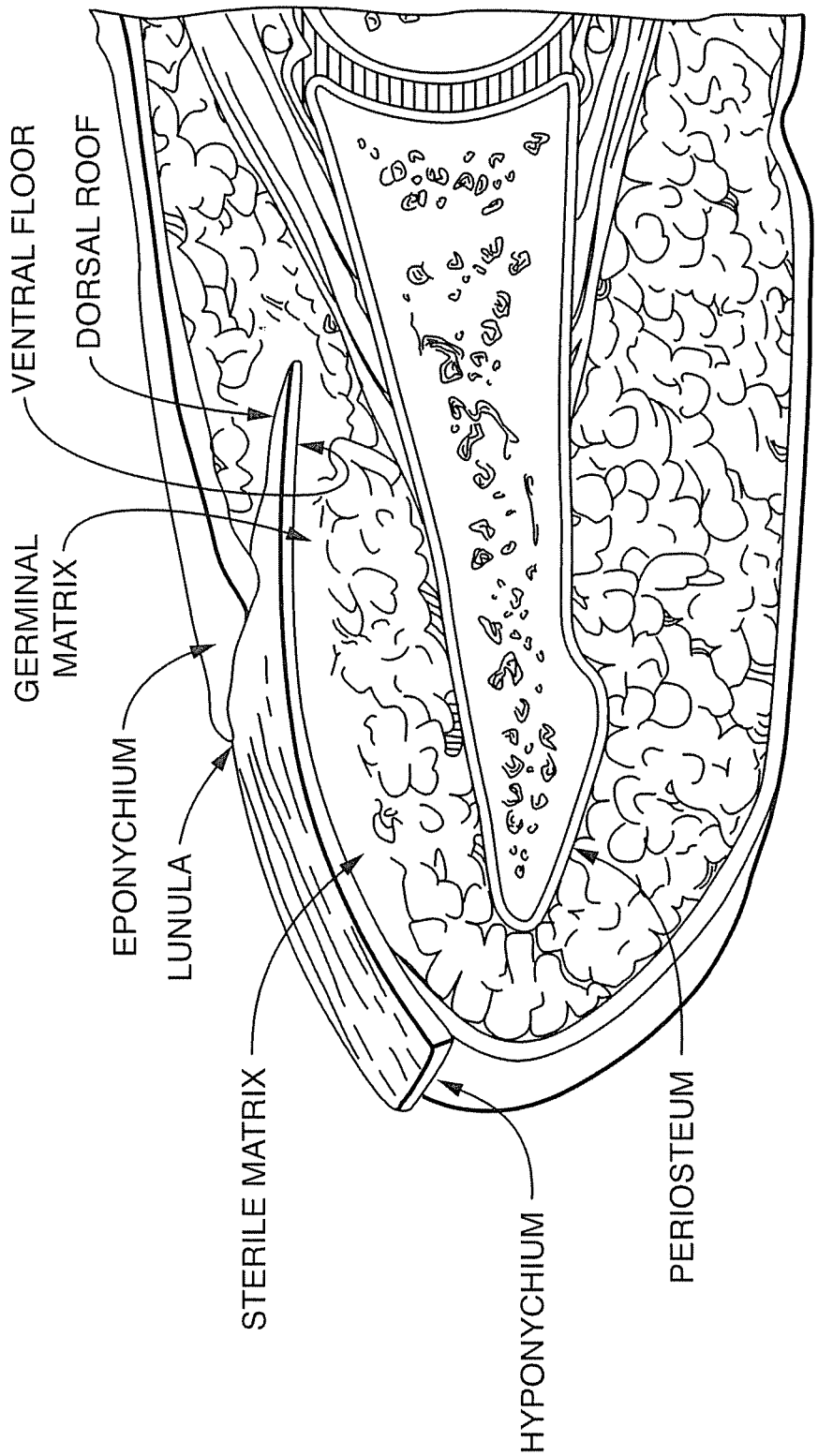
FIG. 8 is a diagram depicting the nail complex, showing the nail bed (matrix), the nail plate and the perionychium.

This example is provided to illustrate how a practitioner's evaluation aids and informs in evaluating whether to increase, reduce or continue a particular treatment dose, mode of irradiation. Making reference to FIG. 8, the healthy nail plate is hard and translucent, and is composed of dead keratin. The plate is surrounded by the perionychium, which consists of proximal and lateral nail folds, and the hyponychium, the area beneath the free edge of the nail. The nail bed is beneath the nail plate and contains the blood vessels and nerves. Contained in the nail bed is the germinal matrix, which produces most of the nails keratinized volume, and the sterile matrix. This matrix is the "root" of the nail, and its most distal portion is visible on many nails as the half-moon shaped structure called the lunula.

Figure 9:
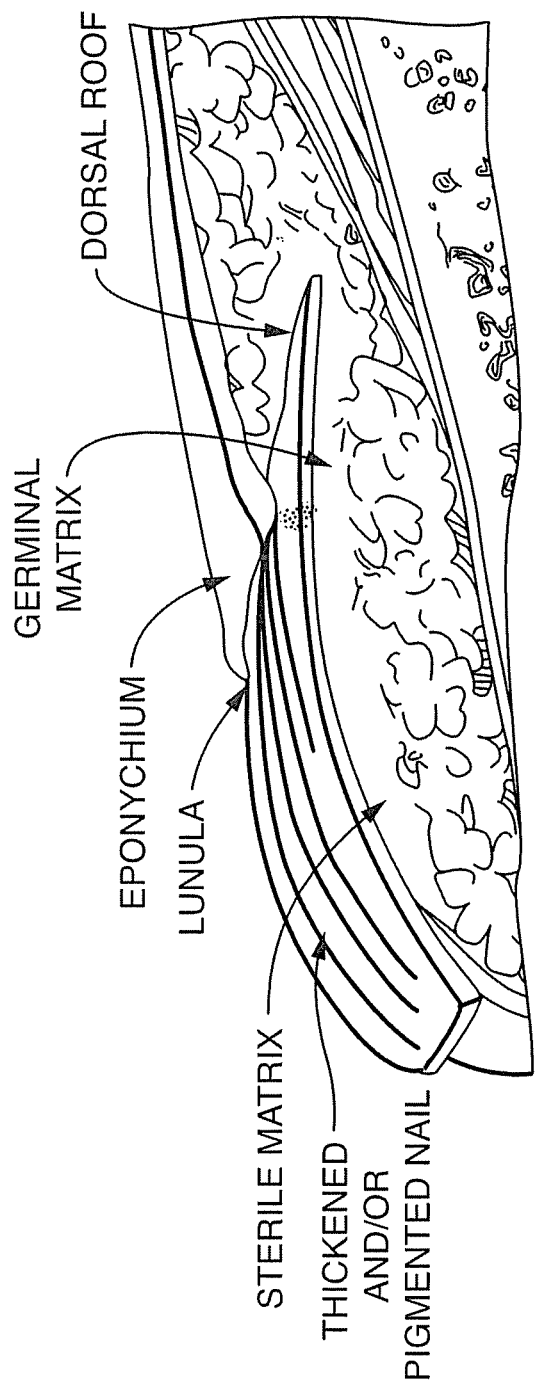
FIG. 9 is a diagram depicting the nail of a typical onychomycosis patient showing the plate, bed (sterile matrix and germinal matrix) and nail fold (lunula growing out under the eponychium) area beginning to improve in the weeks following initial treatment according to one of the embodiments of the disclosure.

FIG. 9 shows the diagram of a typical onychomycosis patient's nail evidencing the effectiveness of the treatment by the presence of healthy nail growth. The practitioner will recognize that the clean and "unifected" portion of the newly growing nail plate (proximal to the germinal matrix, eponychium and lunula) will not automatically need to be irradiated in subsequent treatments. Hence, the irradiation spot should potentially be aimed preferentially or only at the diseased areas, that are still impregnated with the pathogen(s).

Figure 10:
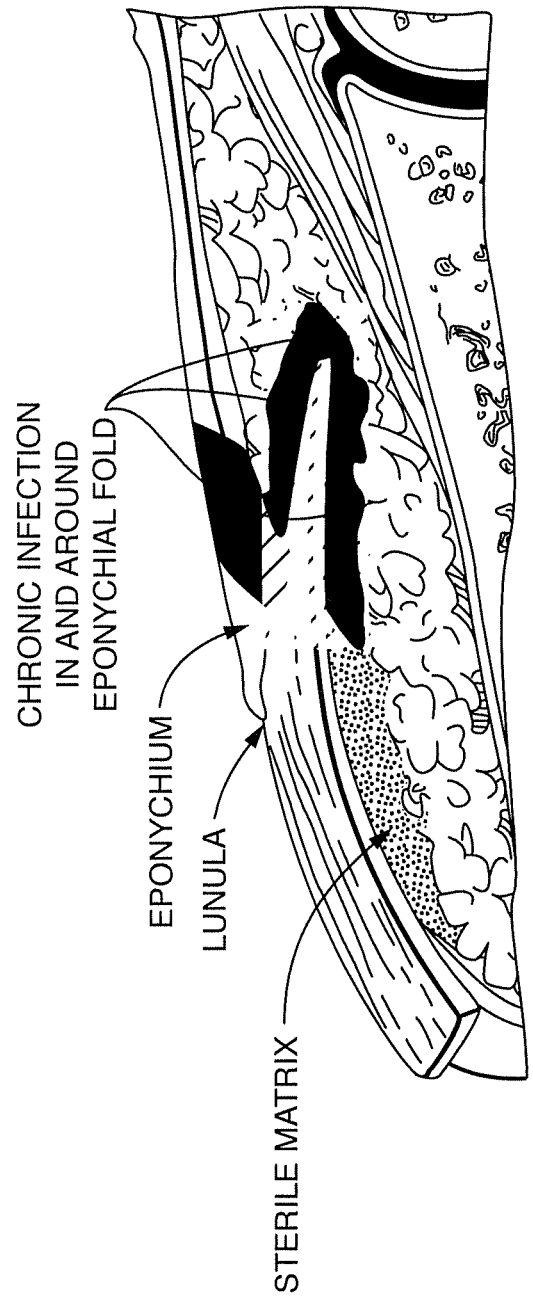
FIG. 10 is a diagram showing a chronically infected nail also showing characteristic features associated with chronic paronychia (e.g., superficial infections in the epidermis bordering the nails).

In certain instances nails infected with onychomycosis are inherently "thicker" (because of dystrophic growth) or "colored" (because of the chroma produced by the fungal pathogen) (see, FIG. 10) and may require a longer lasing time (higher energy density) to penetrate through the nail plate to the infected areas of the bed (sterile matrix and germinal matrix) and nail fold lunula growing out under the Eponychium). As shown in FIG. 10, paronychial infections can develop when a disruption occurs between the seal of the proximal nail fold and the nail plate that allows a portal of entry for invading organisms. Chronic paronychia as a rule, causes swollen, red, tender and boggy nail folds where the symptoms of the disease present for six weeks or longer and are concomitant with long term onychomycosis.

Figure 15:
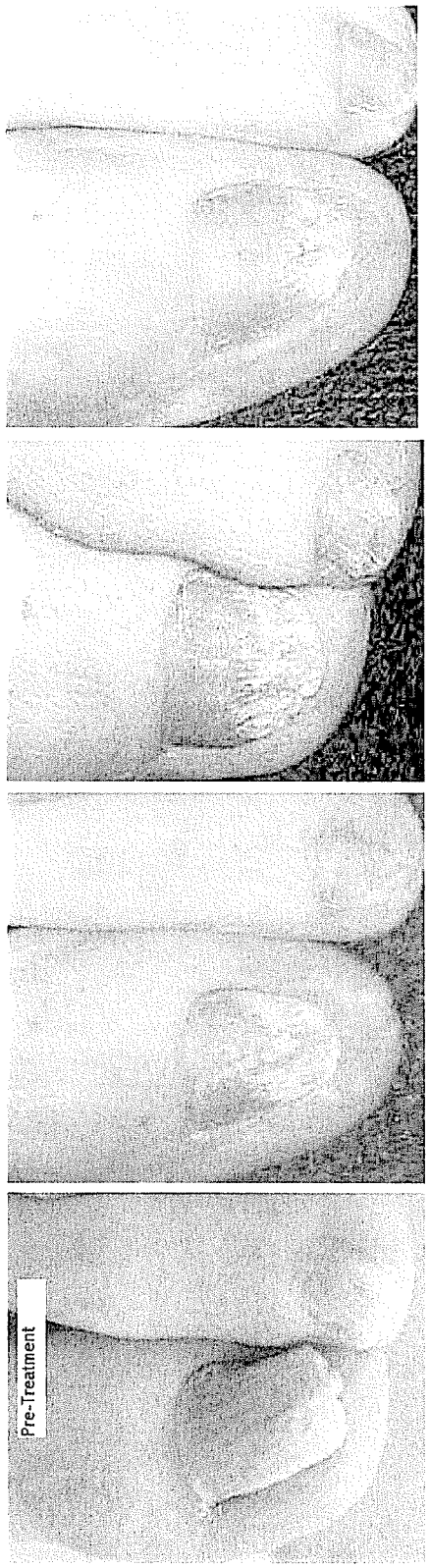
FIG. 15 is a composite showing the improvement over time in the appearance of the nail of a typical onychomycosis patient treated according to the methods of the disclosure.

FIG. 15 is a composite showing the improvement over time in the appearance of the nail of a typical onychomycosis patient treated according to the methods of the disclosure.

Figure 11:
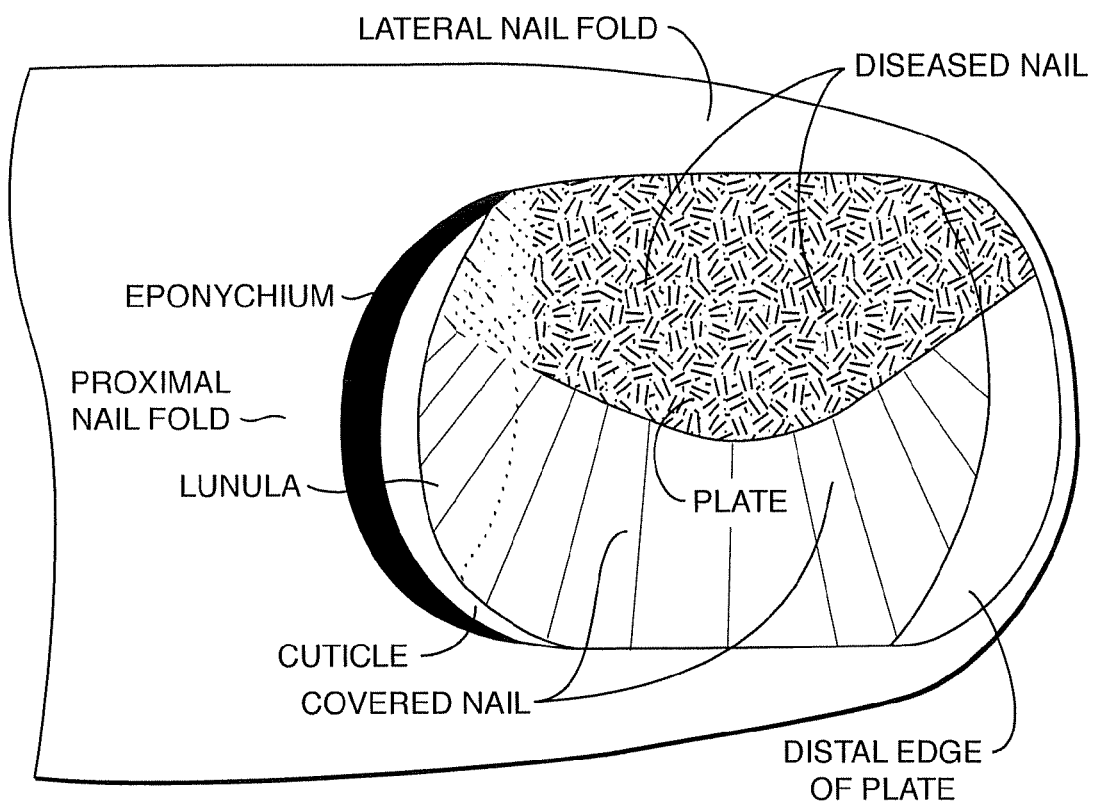
FIG. 11 is a diagram depicting the nail of certain onychomycosis patients showing different discrete areas of the nail infected with a pathogen, and other areas that are completely clean where the healthy portion of the nail plate is still hard and translucent.

As shown in FIG. 11, in patients with concurrent chronic paronychia, the "spot size" of the laser treatment area should be expanded to cover the infected paronychial regions to be sure that all of the pathogen infected areas of the nail complex are treated with the NIMELS laser.

In certain cases, onychomycosis patients may have different discrete areas of the nail infected with a pathogen, and other areas that are completely clean where the healthy portion of the nail plate is still hard and translucent (ref. to FIG. 11). This may be in a vertical or horizontal pattern and can reach to and beyond the lunula growing out under the eponychium. In these cases, the practitioner will recognize that the clean and "unifected" portion of the nail plate will not automatically need to be irradiated, and the spot size and concominent laser dosimetry will be adjusted accordingly to allow successful treatment without damaging any part of the healthy nail complex. Also, the healthy part of the nail could be covered with an opaque substance to allow for a larger irradiation spot from the laser, if the geometry of the infected part of the nail could not be adequately treated with simply a "smaller spot".

EXAMPLE X

Reciprocal Progression Analysis for In Vivo NIMELS Therapy with Output Power of Laser Fixed at 3.0 Watts Combined: Both 870 and 930 at 1.5 W To illustrate typical analysis performed for in vivo therapy, the following example assumed the use of a laser with a power output of 3 W to emit energy with λ=870 and 930 nm.

TABLE XX

Dual Wavelengths λ = 870 and 930 nm.

| OUTPUT POWER (W) | BEAM SPOT (CM) | AREA OF SPOT (CM2) | TIME (SEC) | TOTAL ENERGY JOULES | ENERGY DENSITY (J/CM$^2$) | POWER DENSITY (W/CM$^2$) |
|---|---|---|---|---|---|---|
| 3.0 | 1.2 | 1.13 | 154 | 462 | 408 | 2.65 |
| 3.0 | 1.3 | 1.33 | 180 | 540 | 407 | 2.26 |
| 3.0 | 1.4 | 1.54 | 210 | 630 | 409 | 1.95 |
| 3.0 | 1.5 | 1.77 | 240 | 720 | 407 | 1.70 |
| 3.0 | 1.6 | 2.01 | 272 | 816 | 406 | 1.49 |
| 3.0 | 1.7 | 2.27 | 309 | 927 | 408 | 1.32 |
| 3.0 | 1.8 | 2.54 | 345 | 1035 | 407 | 1.18 |
| 3.0 | 1.9 | 2.84 | 382 | 1146 | 404 | 1.06 |
| 3.0 | 2 | 3.14 | 428 | 1284 | 409 | 0.95 |
| 3.0 | 2.1 | 3.46 | 472 | 1416 | 409 | 0.87 |
| 3.0 | 2.2 | 3.80 | 514 | 1542 | 406 | 0.79 |

Figure 14:
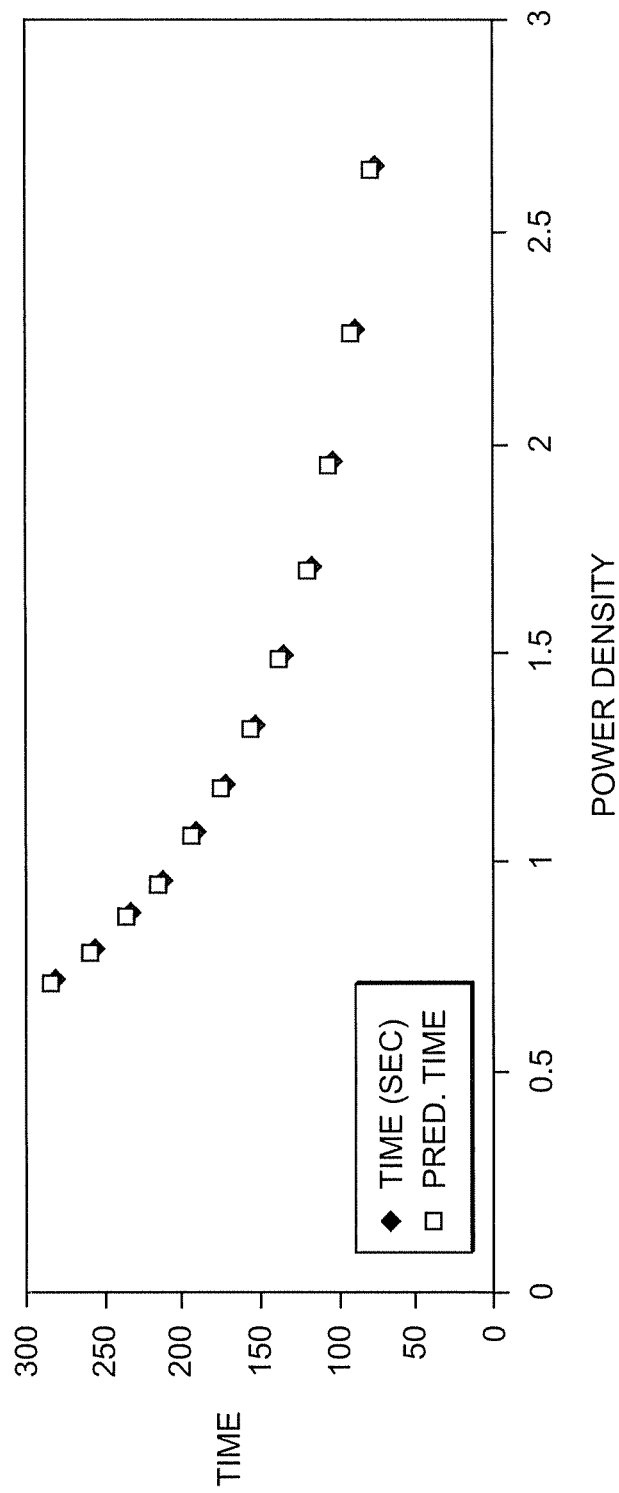
FIG. 14 is a graph showing the Tn function for given spot-size parameters (1.2-2.2 cm diameter), treatment time parameters derived by dividing an energy density of 205 J/cm$^2$ by the power density, at a laser output power of 3.0 Watts.

In this context, Tn=409 (Energy density)/Power Density. FIG. 14, shows derived values for a given spot-size (1.2-2.2 cm diameter). Treatment time for NIMELS therapy was derived dividing an Energy Density of 409 J/cm² by the Power Density, at a laser output power of 3.0 Watts. Hence, NIMELS (Time) Factor=Tn=409/Power Density.

EXAMPLE XI

Reciprocal Progression Analysis for In Vivo NIMELS Therapy with Output Power of Laser Fixed at 3.0 Watts and Wavelength at 930 nm To illustrate typical analysis performed for in vivo therapy, the following example assumed the use of a laser with a power output of 3 W to emit energy with λ=930 nm.

TABLE XXI

Single Wavelength λ = 930 nm.

| OUTPUT POWER (W) | BEAM SPOT (CM) | AREA OF SPOT (CM²) | TIME (SEC) | TOTAL ENERGY JOULES | ENERGY DENSITY (J/CM²) | POWER DENSITY (W/CM²) |
|---|---|---|---|---|---|---|
| 3.0 | 1.2 | 1.13 | 77 | 231 | 204 | 2.65 |
| 3.0 | 1.3 | 1.33 | 90 | 270 | 203 | 2.26 |
| 3.0 | 1.4 | 1.54 | 105 | 315 | 205 | 1.95 |
| 3.0 | 1.5 | 1.77 | 120 | 360 | 204 | 1.70 |
| 3.0 | 1.6 | 2.01 | 137 | 411 | 204 | 1.49 |
| 3.0 | 1.7 | 2.27 | 155 | 465 | 205 | 1.32 |
| 3.0 | 1.8 | 2.54 | 172 | 516 | 203 | 1.18 |
| 3.0 | 1.9 | 2.84 | 194 | 582 | 205 | 1.06 |
| 3.0 | 2 | 3.14 | 214 | 642 | 204 | 0.95 |
| 3.0 | 2.1 | 3.46 | 233 | 699 | 202 | 0.87 |
| 3.0 | 2.2 | 3.80 | 256 | 768 | 202 | 0.79 |

On the basis of the observed value (see, data above in Table XXI) it is found that Tn=205 (energy density)/power density. Hence, within the given spot-size parameters (1.2-2.2 cm diameter), treatment time for NIMELS therapy can be simply derived dividing an energy density of 205 J/cm² by the power density, at a laser output power of 3.0 Watts (see FIG. 13). Hence, NIMELS (Time) Factor=Tn=205/Power Density.

This novel algorithm for NIMELS dosimetry calculations concerns the quantification of a known and constant NIMELS threshold energy density for an antimicrobial and/or antifungal phenomenon based on the unique wavelengths of energy delivery being simultaneous (A=870 nm and 930 nm together), or using a 930 nm wavelength alone.

Therefore, it is desirable to NIMELS antimicrobial therapy that this method of (Energy Density) quantification is conserved and the novel value of the NIMELS Factor (Tn) is used to calculate the necessary, parabolic reciprocal correlations for safe and effective dosimetry values.

This NIMEL method of temporal and reciprocal dosimetry should also hold true for differences in laser output power (between 1 W-5 W) as long as any quantifiable thermal increase, thermal increase time durations, and photobiological events in the tissues are kept below any irreversible damage threshold values.

EXAMPLE XII

NIMELS Therapy Used with Exemplary Medical Devices

The following examples, described with particular reference to FIGS. 16-22, are provided to illustrate the application of the NIMEL technology in the medical devices area as discussed above. Accordingly, the embodiments described are provided as representative examples. One of skill will appreciate that multiple permutations and variations exploiting the underlying NIMEL methodology may be devised.

Figure 16:
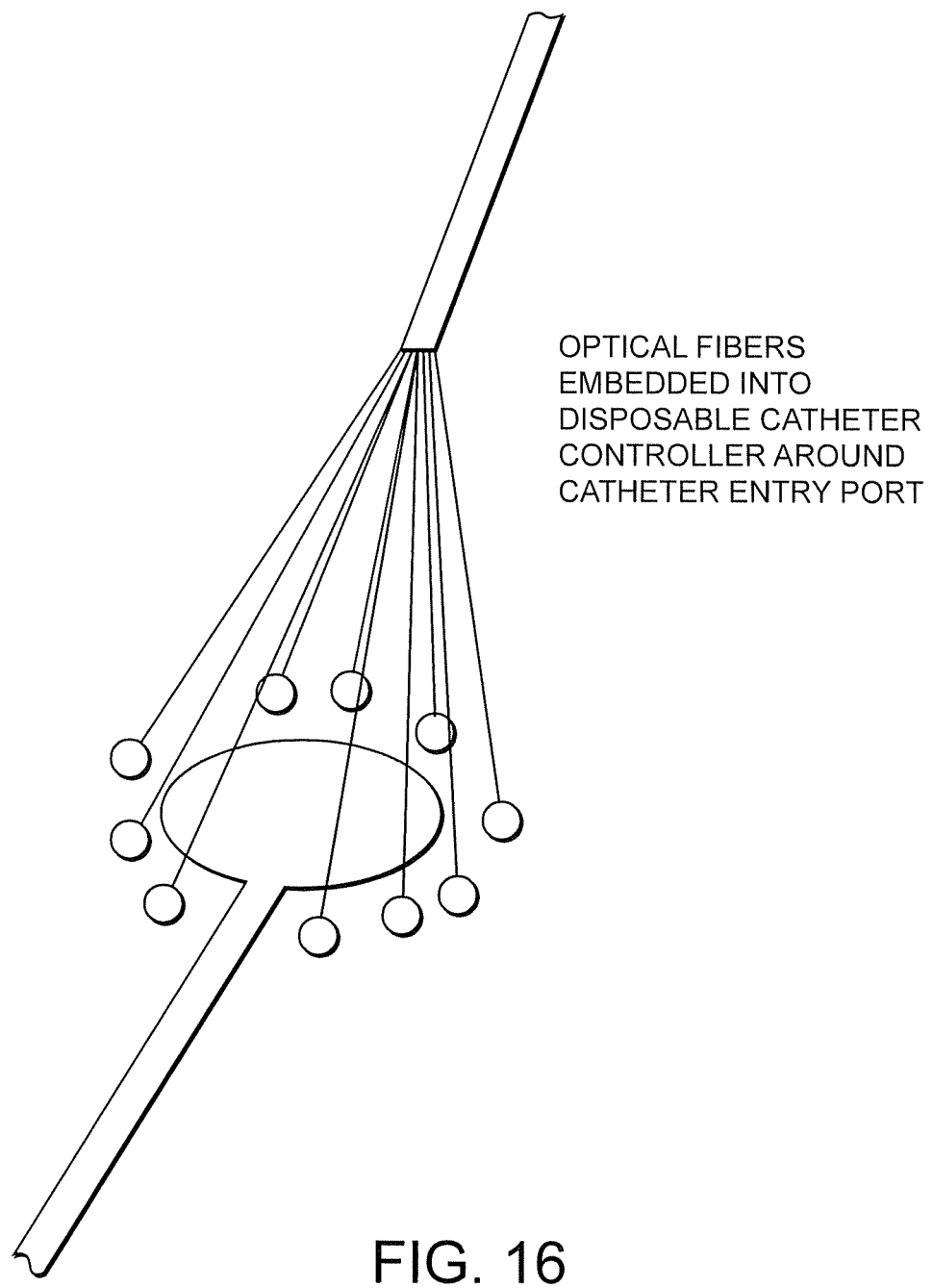
FIG. 16 shows an embodiment of a NIMELS Optical Catheter Controller including delivery assembly configured as multiple optical fibers embedded into the catheter controller around a catheter entry port placed on a patient.
Figure 17:
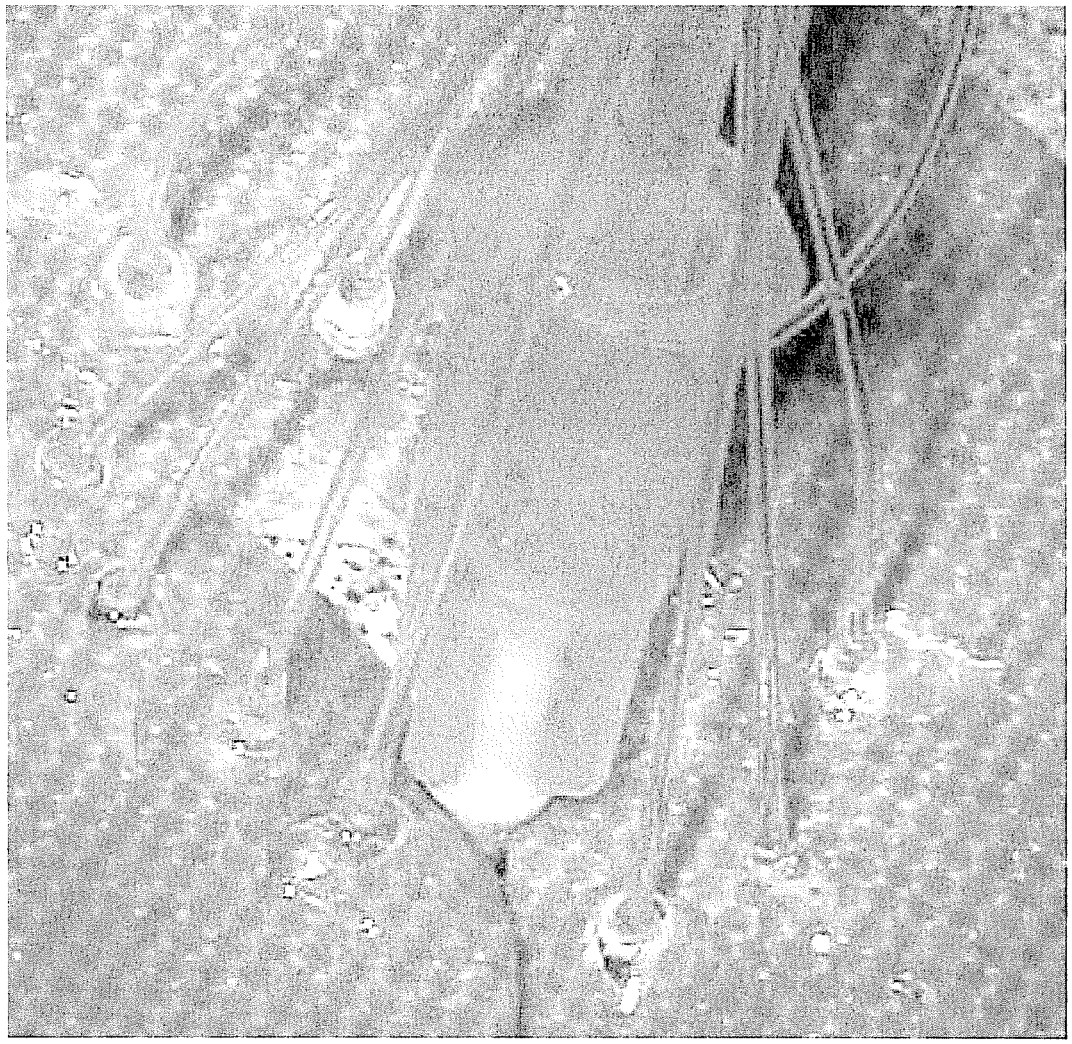
FIG. 17 shows a physical model constructed to simulate the embodiment of FIG. 16.

FIG. 16 shows an embodiment of a NIMELS Optical Catheter Controller including delivery assembly configured as multiple optical fibers embedded into a catheter controller around a catheter entry port placed on a patient. FIG. 17 shows a physical model constructed to simulate the embodiment of FIG. 16.

FIGS. 16 and 17 show a connectable adapter whereby a spray of optical fibers are imbedded within a disposable percutaneous device controller, and distally connected to a NIMEL laser system. In many different variations depending on the size of the percutaneous device, a plurality of optical fiber sprays are imbedded in a circular (or other) overlapping pattern, to enable irradiation on the percutaneous wound for the percutaneous device. According to this embodiment of the invention, the fibers are bundled together at one end, where they can be connected to NIMELS laser system, and at the other end unrestrained to flare outwardly forming a spray, to embed in a necessary pattern in the percutaneous device controller bandage.

Figure 18:
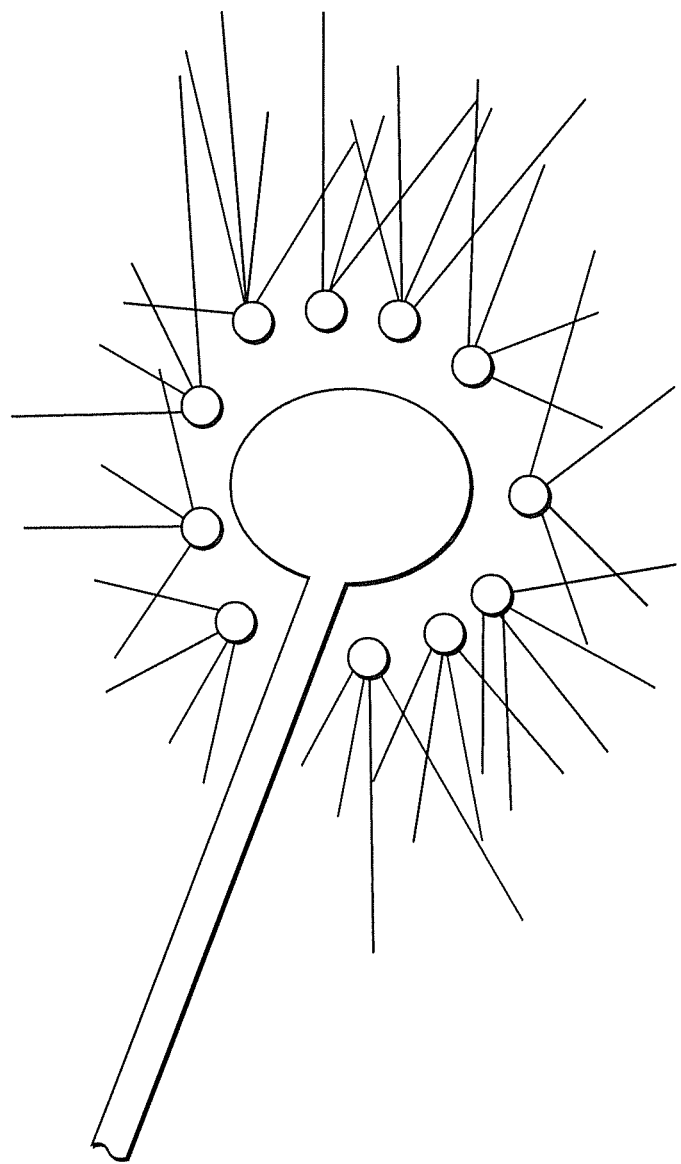
FIG. 18 depicts the underside of a NIMELS Optical Catheter Controller similar to FIG. 16.
Figure 19:
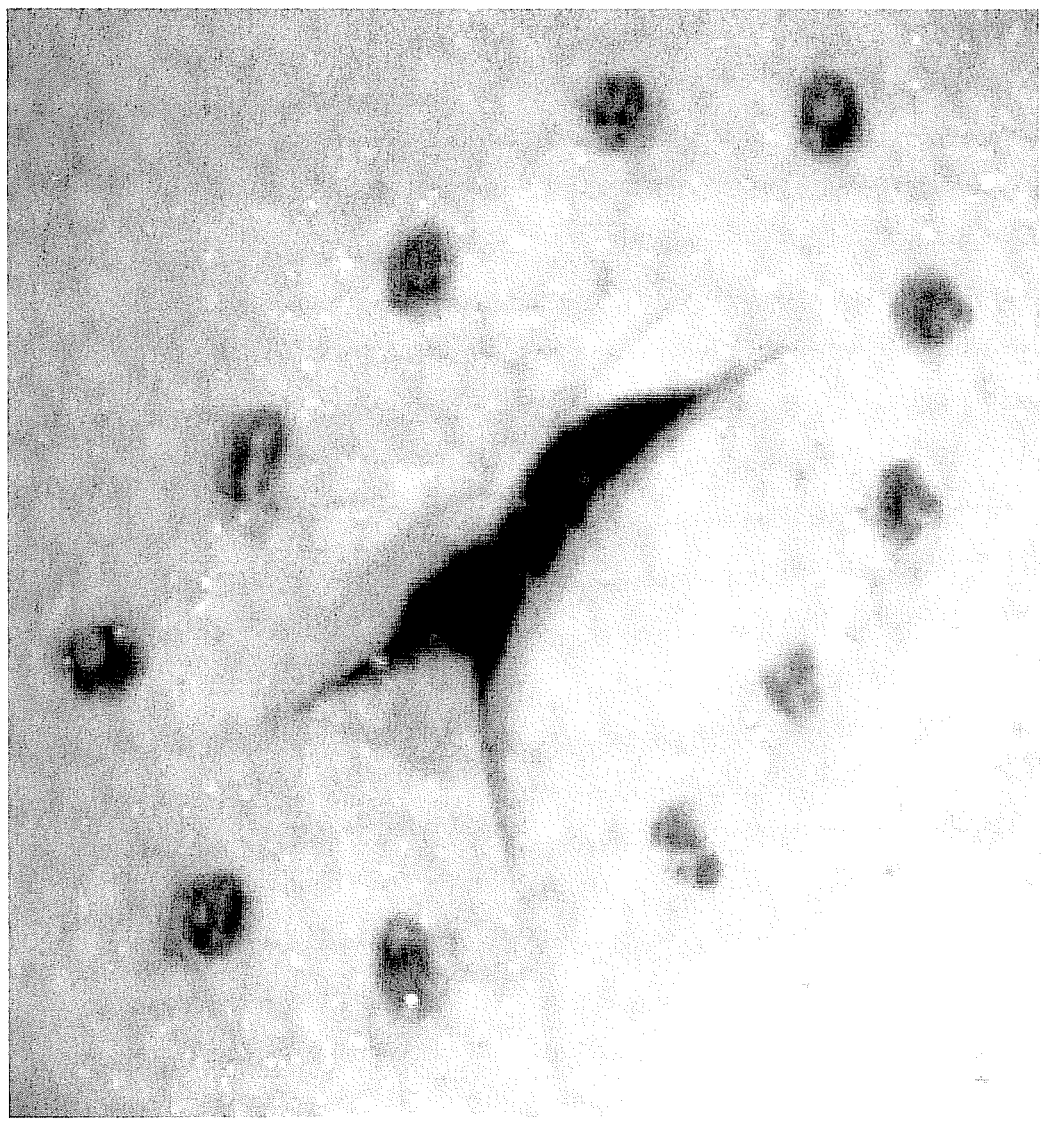
FIG. 19 shows a physical model according to FIG. 18, with the optical fibers removed.

FIG. 18 depicts the underside of a NIMELS Optical Catheter Controller similar to FIG. 16. FIG. 19 shows a physical model according to FIG. 18, with the optical fibers removed.

FIGS. 18 and 19 illustrate the illumination of optical fiber arrays for the irradiation of percutaneous wounds with percutaneous device controllers. The adapter carries the bundled end of the optical fibers at one end, and is formed to engage an adapter connected to a NIMELS laser system. The fiber optic can transmit NIMELS energy to a variety and plurality of different locations throughout the percutaneous device controller, and the percutaneous device itself. The fiber optic cable can include a plurality of optical fibers, each of which individually terminates at one of a plurality of sites in and around the percutaneous device controller and the percutaneous device itself. This can include a stepped or Bragg graded fiber for the internal lumen irradiation of a percutaneous device. Alternatively, the optical fibers can individually terminate at desired, e.g., evenly spaced, locations throughout the device to illuminate a region of the percutaneous device controller uniformly.

Figure 20:
FIG. 20 is prototype enabled side view of a NIMELS Optical Microbial Catheter Controller according to the present disclosure.
Figure 21:
FIG. 21 is an additional view of the prototype of FIG. 20.

FIG. 20 is prototype enabled side view of a NIMELS Optical Microbial Catheter Controller according to the present disclosure. FIG. 21 is an additional view of the prototype of FIG. 20.

FIGS. 20 and 21 illustrate a Radiation Dispersion Bandage or Optical Percutaneous Device Controller for use as an adjunctive treatment for an infected percutaneous device or to prevent infection and colonization of a percutaneous device. The device can alternatively include flexible illuminators for the external and internal phototherapy of a percutaneous device controller and/or percutaneous device itself. The illuminators may be formed so as to be imbedded or wrapped in or around a percutaneous device controller and or percutaneous device itself. In another configuration, the illuminators may be actively or passively cooled so the percutaneous wound, skin, and or device itself remains below a desired temperature.

Also, a flexible band or belt may be provided with the percutaneous device controller to permit the device to be held or contoured to a desired body surface for the adequate positioning and illumination of the percutaneous device. The Optical Percutaneous Device Controller can be designed (e.g., configured and arranged) to swathe tightly around vascular and non-vascular percutaneous devices, providing extended antimicrobial environments (with NIMELS energy) for extended periods of time.

Figure 22:
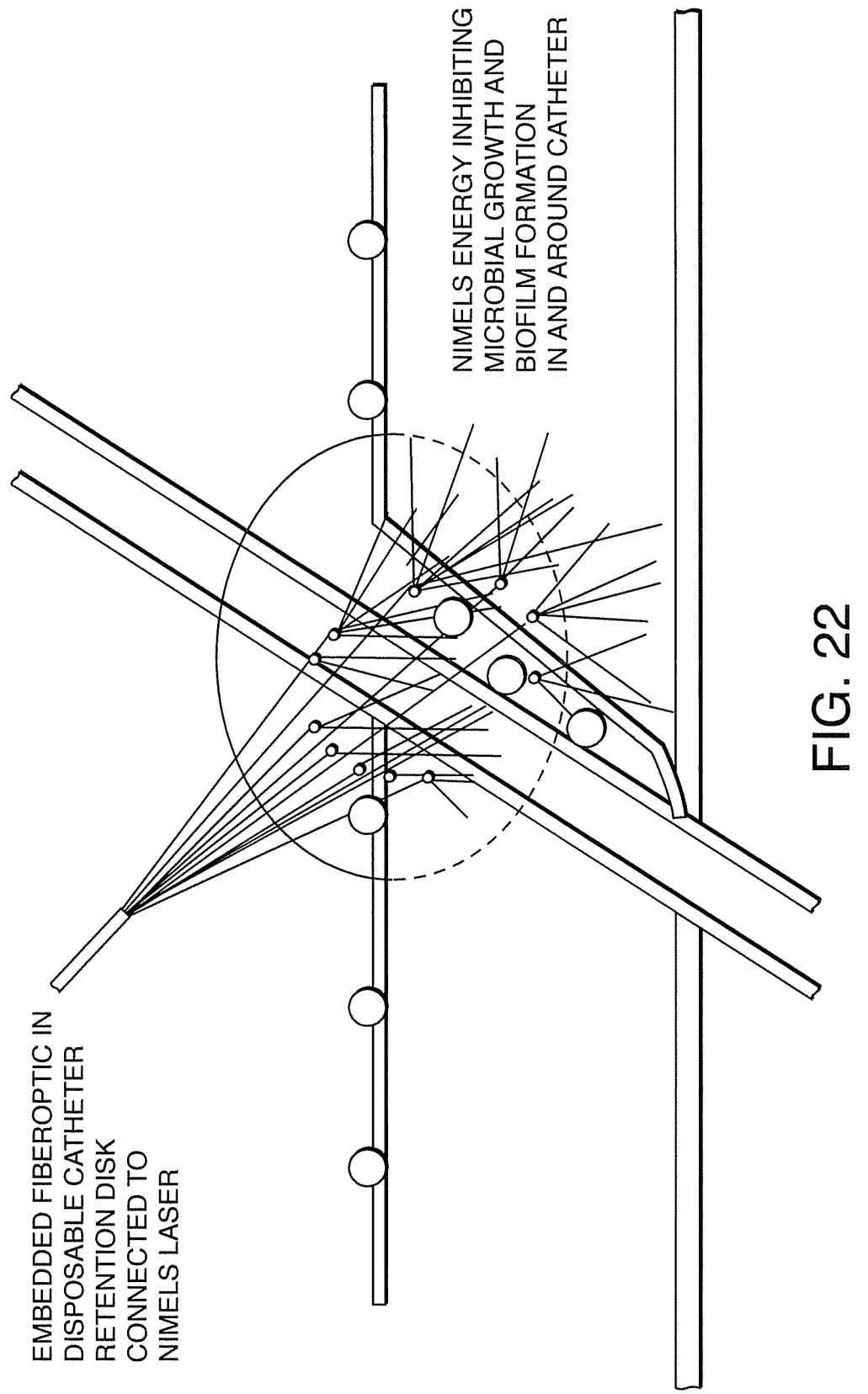
FIG. 22 is a further view of a NIMELS Optical Microbial Catheter Controller according to the present disclosure.

FIG. 22 is a further view of a NIMELS Optical Microbial Catheter Controller according to the present disclosure.

As noted previously, a delivery assembly used according to the present disclosure may take forms other than optical fibers. For example, hollow waveguides may be used for the delivery assembly in certain embodiments. Other size and shapes for the deliver assembly, e.g., assembly 14 in FIG. 2, may also be employed based on the requirements of the application site. In exemplary embodiments, the delivery assembly 14 can be configured for free space or free beam application of the optical radiation, e.g., making use of available transmission through tissue at NIMELS wavelengths described herein. For example, at 930 nm (and to a similar degree, 870 nm), the applied optical radiation can penetrate patient tissue by up to 1 cm or more. Such embodiments may be particularly well suited for use with in vivo medical devices as described below. Suitable collimating and/or aperture stop optical elements may be used.

Figure 13:
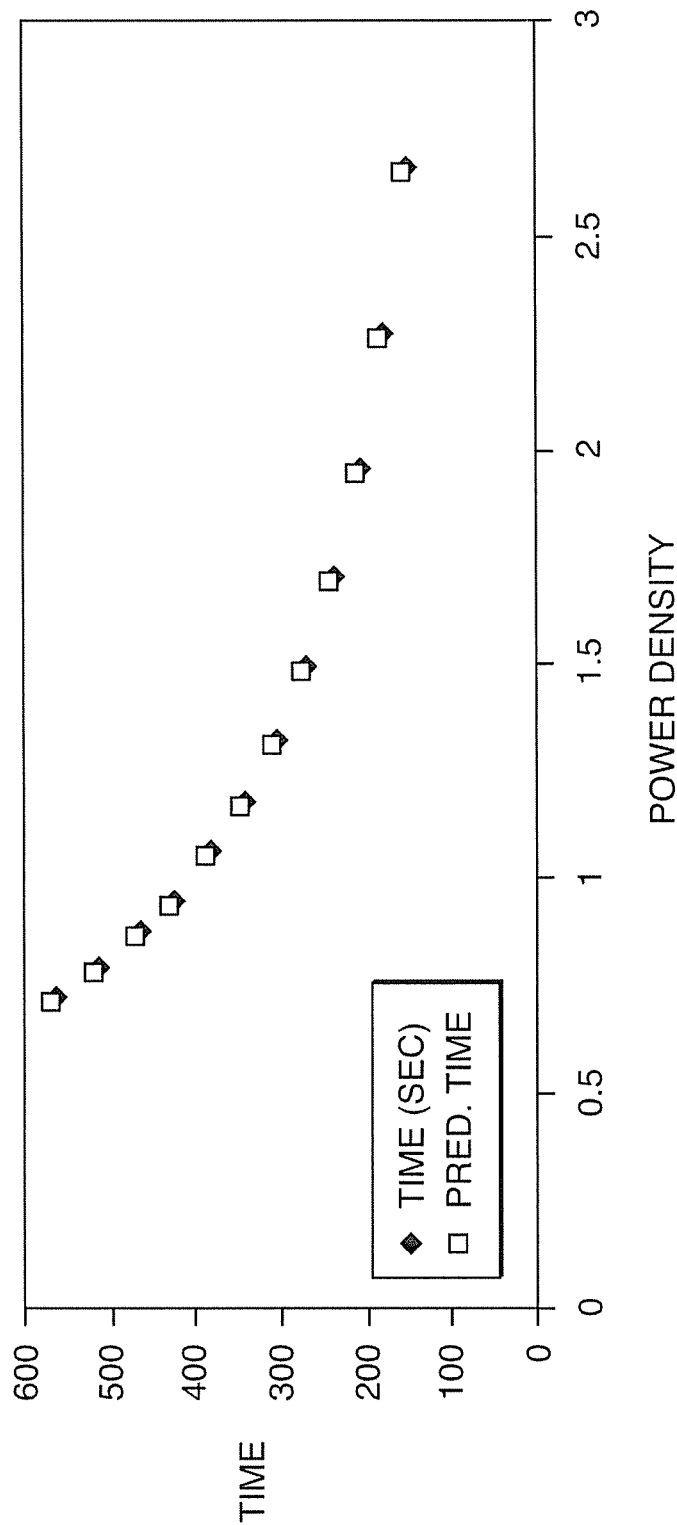
FIG. 13 is a graph showing the Tn function for given spot-size parameters (1.2-2.2 cm diameter), treatment time parameters derived by dividing an energy density of 409 J/cm$^2$ by the power density, at a laser output power of 3.0 Watts.

Accordingly, applications of NIMELS techniques of the present disclosure can be used with medical devices including, the but not limited to, IV Catheters, such as PICC sites, Central Venous (CV) Lines, Arterial Catheter, Peripheral Catheters, Dialysis Catheters, External fixator pins, Peritoneal dialysis catheters, Epidural catheters, Chest tubes, Gastronomy feeding tubes as illustrated in FIG. 13.

EXAMPLE XIII

In Vitro Safety Testing—Mammalian Cells

Conventional mouse 3T3 fibroblasts were used to determine whether mammalian cells were injured by the NIMELS laser treatment. Treatment plates containing a standardized quantity of fibroblasts were exposed to the NIMELS laser; control plates containing the same quantity of fibroblasts were held at room temperature for the duration of laser treatment.

After treatment, the cells were allowed to attach to their plates for three hours in a 37° C. incubator. The cells were then extracted from the plates and examined for morphology and viability. While there were morphological changes observed in the treated fibroblasts, the viability of the treated and control plates showed no significant difference. These results indicate that any cell damage (as demonstrated by morphological changes) did not affect cellular viability.

An additional in vitro study was undertaken to test for thermal and optical safety to mouse 3T3 fibroblast tissue when exposed to NIMELS laser dosimetry shown to be lethal to bacteria in vitro. Fibroblast cells were inoculated with 500,000 CFU of *E. coli* K-12. This "infected" sample was treated with the microbial-lethal laser dosimetry ascertained from prior studies (see, supra). Three hours after treatment, these fibroblast cells appeared viable in shape and morphology. In cultures performed at 16 hours post-treatment, there was no bacterial growth in standard agar and mammalian growth serum medium.

EXAMPLE XIV

In Vivo Safety Testing—Mammalian Cells

Based on the in vitro results, a study was performed in mice to determine the safety of the NIMELS laser at these wavelengths in an animal model.

A pilot dosimetry study was conducted using a NIMELS laser on the dorsal skin of the FVB (Friend leukemia virus B strain) mouse strain. Six groups of four mice each were used. This included the testing of laser intensity, energy level, power density (PD), exposure time and spot size. Observations were made on the mice on the day of study (day 0), with follow up observations conducted on day 1 and 2. The mice were sacrificed on day 2 and sections from the laser-exposed region were prepared for histological examination by paraffin embedding followed by Hematoxylin and Eosin (H&E) staining.

All animal deaths, serious morbidity and visible scarring of the skin occurred in animals where energy (range 888-3034 J), power density (range 2.04-3.82) levels or exposure time were used that far exceeded those contemplated above for use with mammals according to the invention.

Thirty-four (34) specimens were studied microscopically. All came from animals that survived the initial treatment and lived through the observation period. The histology revealed that 28 of the 34 specimens showed no histological abnormality, of which 6 were controls, and 22 had been exposed to laser energies ranging from 360 J to 1776 J and PD ranging from 1.02 to 2.72.

There were six specimens that demonstrated positive histology, three of which had been exposed to laser energies far greater than 750 J (ranging from 1332 J to 1998 J). Of the remainder, one had been exposed to extremely high power density (PD 3.82, 444 J) and one was subjected to significantly prolonged exposure time (4 minute exposure with 930 nm, 750 J). In the remaining specimen, the exposure factors were within the range anticipated for human use.

The intensity of histological changes was carefully noted. It is noteworthy that in none of the specimens in which there were histological changes noted, even those subjected to extreme exposures, none of the findings extended subcutaneously to the underlying muscular layer or beyond. The changes were extremely superficial, penetrating to a depth of less than 90 microns. The surface ulcerations noted were recognizable only after careful microscopic search and were less than 60 microns in diameter and 40 microns in depth. Therefore, all changes were considered minor and of little clinical consequence.

A strong correlation with adverse events was noted with energy levels used (Joules), where all events increase in number and intensity as the J level increased. With one exception, no major adverse outcomes were noted when laser energy of 750 J or less was used. In only one animal was there some evidence of skin scarring noted at 750 J and that occurred when the duration of the laser exposure was extended to twice the usual time anticipated for use in mammals (e.g., humans).

The study revealed that there was no apparent damage to the skin or underlying tissue in the majority of the animals. Severe morbidity was confined to the animals in which very high energy levels were employed. The number and intensity of all serious adverse outcomes related to the intensity of the exposure, all occurring when physical parameters were used that far exceeded anticipated human use.

Positive histological findings were encountered across a broad range of parameters, and were clearly more prominent when higher energy levels or higher power density was employed. Most importantly, where levels were employed that were within the range of anticipated use in mammals, the findings were either normal or, if abnormal, were of an extremely minor nature, recognizable only after extensive microscopic search.

The study underscores the necessity of not only monitoring the energy levels (J) employed, but the necessity of maintaining proper control of exposure time and laser beam spot size, each of which will significantly affect power density (PD).

EXAMPLE XV

In Vivo Safety Testing—Human Patient

Following the in vitro fibroblast studies, the inventor performed a dosimetry titration on himself to ascertain the safe, maximum level of energy and time of exposure that could be delivered to human dermal tissue without burning or otherwise damaging the irradiated tissues.

The methodology he used was to irradiate his great toe for varying lengths of time and power settings with the NIMELS laser. The results of this self-exposure experiment are described below.

TABLE XXII

Combined Wavelength Dosimetries

| PARAMETERS | OUTPUT POWER (W) | BEAM SPOT (CM) | AREA OF SPOT (CM$^2$) | TIME (SEC) | TOTAL ENERGY JOULES | ENERGY DENSITY (J/CM$^2$) | POWER DENSITY (W/CM$^2$) |
|---|---|---|---|---|---|---|---|
| 870 nm | 1.5 | 1.5 | 1.77 | 250 | 375 | 212 | 0.85 |
| 930 nm | 1.5 | 1.5 | 1.77 | 250 | 375 | 212 | 0.85 |
| Combined | 3.0 | 1.5 | 1.77 | 250 | 750 | 424 | 1.70 |

TABLE XXIII

Dosimetry at λ = 930 nm

| PARAMETERS | OUTPUT POWER (W) | BEAM SPOT (CM) | AREA OF SPOT (CM2) | TIME (SEC) | TOTAL ENERGY JOULES | ENERGY DENSITY (J/CM$^2$) | POWER DENSITY (W/CM$^2$) |
|---|---|---|---|---|---|---|---|
| 930 nm | 3.0 | 1.5 | 1.77 | 120 | 360 | 204 | 1.70 |

Time/Temperature assessments were charted to ensure the thermal safety of these laser energies on human dermal tissues (data not shown). In one laser procedure, he exposed his great toe to both 870 nm and 930 nm for up to 233 seconds, while measuring toenail surface temperature with a laser infrared thermometer. He found that using the above dosimetries, at a surface temperature of 37.5° C., with 870 mm and 930 nm together with a combined Power Density of 1.70 W/cm$^2$, pain resulted and the laser was turned off.

In a second laser procedure, he exposed his great toe to 930 nm for up to 142 seconds, while again measuring toenail surface temperature with a laser infrared thermometer. He found that, at a surface temperature of 36° C., with 930 nm alone at a Power Density of 1.70 W/cm$^2$, pain resulted and the laser was turned off.

EXAMPLE XVI

In Vivo Safety Testing—Limited Clinical Pilot Study

Following the experiment above, additional patients with onychomycosis of the feet were treated. These patients were all unpaid volunteers, who provided signed informed consent. The principle goal of this limited pilot study was to achieve the same level of fungal decontamination in vivo, as was obtained in vitro with the NIMELS laser device. We also decided to apply the maximum time exposure and temperature limit that was tolerated by the inventor during his self-exposure experiment.

In a highly controlled and monitored environment, three to five laser exposure procedures were performed on each subject. Four subjects were recruited and underwent the treatment. Subjects provided signed informed consent, were not compensated, and were informed they could withdraw at any time, even during a procedure.

The dosimetry that was used for the treatment of the first subject was the same as that used during the inventor's self-exposure (shown above). The temperature parameters on the surface of the nail also were equivalent to the temperatures found by the inventor on self-exposure.

The treated toes showed significantly reduced Tinea pedis and scaling surrounding the nail beds, which indicated a decontamination of the nail plate that was acting as a reservoir for the fungus. The control nails were scraped with a cross-cut tissue bur, and the shavings were saved to be plated on mycological media. The treated nails were scraped and plated in the exact same manner.

For culturing the nail scrapings, Sabouraud dextrose agar (2% dextrose) medium was prepared with the following additions: chloramphenicol (0.04 mg/ml), for general fungal testing; chloramphenicol (0.04 mg/ml) and cycloheximide (0.4 g/ml), which is selective for dermatophytes; chloramphenicol (0.04 mg/ml) and griseofulvin (20 μg/ml), which served as a negative control for fungal growth.

Nine-day mycological results for Treatment #1 and Treatment #2 (performed three days after Treatment #1) were the same, with a dermatophyte growing on the control toenail plates, and no growth on the treated toenail plates. Treated plates did not show any growth whereas untreated control culture plates showed significant growth.

The first subject was followed for 120 days, and received four treatments under the same protocol. FIG. 15 shows a comparison of the pretreatment, 60 days post-treatment and 80 days post-treatment, and 120 days post-treatment toenails. Notably, healthy and non-infected nail plate was covering 50% of the nail area and growing from healthy cuticle after 120 days.

While certain embodiments have been described herein, it will be understood by one skilled in the art that the methods, systems, and apparatus of the present disclosure may be embodied in other specific forms without departing from the spirit thereof. The present embodiments are therefore to be considered in all respects as illustrative and not restrictive of the present disclosure.

What is claimed is:

1. A method for effecting photodamage in a biological contaminant in an illuminated target region of a subject, the method comprising:
   using an optical radiation generation device configured to generate near infrared optical radiation (i) substantially in a first wavelength range from 865 nm to 875 nm and a second wavelength range having a wavelength from 925 nm to 935 nm, and (ii) at a dosimetry including power density of 0.5 W/cm$^2$ to 5 W/cm$^2$ and an energy density from 200 J/cm$^2$ to 700 J/cm$^2$ at the illuminated target region, and a time duration of 50 to 720 seconds, wherein the dosimetry is sufficient to produce photodamage in the biological contaminant;
   using a delivery assembly to cause the optical radiation to be transmitted to illuminate the target region of the subject,
   wherein substantially all of the near infrared optical radiation transmitted from the optical radiation generation device to the target region by the delivery assembly is in the first wavelength range or the second wavelength range, and
   wherein the near infrared optical radiation has a spot size at the target region of at least 1.0 cm; and
   using a controller operatively connected to the optical radiation generation device to control the dosage of the near infrared optical radiation transmitted to the target region of the subject at the dosimetry sufficient to produce photodamage in the biological contaminant.

2. The method of claim 1, wherein the optical radiation source includes a diode laser.

3. The method of claim 1, comprising controlling the radiation to be an output of a succession of radiation pulses or a continuous wave.

4. The method of claim 1, calculating dosimetry needed for treatment of the treatment site.

5. The method of claim 1, comprising transmitting the optical radiation to the target region with a substantially flat-top intensity distribution.

6. The method of claim 1, comprising to providing to the target region a dosimetry comprising a power density from 1 W/cm$^2$ to 4 W/cm$^2$ for treatment of onychomycosis.

7. The method of claim 6, comprising delivering the optical radiation to a plurality of target regions, to simultaneously effect treatment on toes of a patient with onychomycosis.

8. The method of claim 1, wherein optical radiation has a spot size diameter at the target region of between 1.0 cm and 4.0 cm.

9. The method of claim 1, comprising providing to the target region a dosimetry comprising a power density of 0.5 W/cm$^2$ to 2.5 W/cm and an irradiation time of 50 seconds to 500 seconds for treatment of bacteria.

10. The method of claim 1, comprising providing to the target region a dosimetry comprising a power density of 0.5 W/cm$^2$ to 3.5 W/cm$^2$ and an irradiation time of 60 to 600 seconds for treatment of MRSA.

11. The method of claim 1, comprising providing to the target region a dosimetry comprising a power density of 0.5 W/cm$^2$ to 3.5 W/cm$^2$ and an irradiation time of 70 to 700 seconds for treatment of fungi.

12. The method of claim 1, comprising using a flat top lens to receive the optical radiation from the optical radiation generation device and to produce an optical output with a substantially flat-top intensity distribution.

13. A method for effecting photodamage in a drug-resistant biological contaminant in an illuminated target region of a subject, the method comprising:
   applying a drug to the subject, wherein the drug-resistant biological contaminant is resistant to the drug;
   using an optical radiation generation device to generate optical radiation (i) substantially in a first wavelength range from 865 nm to 875 nm and a second wavelength range having a wavelength from 925 nm to 935 nm, and (ii) at a dosimetry including power density of 0.5 W/cm$^2$ to 5 W/cm$^2$ and an energy density from 200 J/cm$^2$ to 700 J/cm$^2$ at the illuminated target region, and a time duration of 50 to 720 seconds, that is sufficient to produce photodamage in the biological contaminant; and
   using a delivery assembly to cause the near infrared optical radiation to be transmitted to the target region, by
      receiving the near infrared optical radiation from the optical radiation generation device and,
      providing the optical radiation to the illuminated target region,
   wherein substantially all of the near infrared optical radiation transmitted from the optical radiation generation device to the target region by the delivery assembly is in the first wavelength range or the second wavelength range,
   wherein the near infrared optical radiation has a spot size at the target region of at least 1.0 cm, and
   wherein the optical intensity is effective for producing photodamage in a biological contaminant at the target region to augment the effectiveness of the drug on the biological contaminant.

14. The method of claim 13, further comprising using a controller operatively connected to the optical radiation generation device to control dosage of the radiation transmitted to the target region at the dosimetry sufficient to produce photodamage in the biological contaminant without causing substantial photothermal or photomechanical damage to biological tissue of the subject at the illuminated target region.

15. The method of claim 13, comprising simultaneously delivering the optical radiation to a plurality of target regions, wherein at each target region the optical radiation has a dosimetry sufficient to produce photodamage in the biological contaminant without intolerable adverse effects on biological tissue at the target region.

16. The method of claim 15, wherein the dosimetry includes power density of 0.5 W/cm$^2$ to 40 W/cm$^2$ and a time duration of 50 to 720 seconds.

17. The method of claim 16, comprising providing to the target region a dosimetry comprising a power density of 0.5 W/cm$^2$ to 2.5 W/cm$^2$ and an irradiation time of 50 seconds to 500 seconds for treatment of bacteria.

18. The system of claim 16, comprising providing to the target region a dosimetry comprising a power density of 0.5 W/cm$^2$ to 3.5 W/cm$^2$ and an irradiation time of 70 to 700 seconds for treatment of fungi.

19. The method of claim 16, comprising providing to the target region a dosimetry comprising a power density of 0.5 W/cm$^2$ to 3.5 W/cm$^2$ and an irradiation time of 60 to 600 seconds for treatment of MRSA.

20. The method of claim 13, wherein the drug comprises an antibiotic.

21. The method of claim 20, wherein the antibiotic comprises a beta-lactam antibiotic.

22. The method of claim 21, wherein the antibiotic comprises a cyclic lipopeptide.

23. The method of claim 20, wherein the antibiotic comprises at least one selected from the list consisting of a beta-lactams antibiotic, a vancomycin, a bacitracin, a macrolide, a ketolide, a lincosamide, a chloramphenicol, a tetracycline, a aminoglycoside, a amphotericn, a cefazolin, a clindamycin, a mupirocin, a sulfonamide, a trimethoprim, a rifampicin, a metronidazole, a quinolone, a novobiocin, a polymixin, a oxazolidinone, a glycylcycline, a cyclic lipopeptide, a pleuromutilin, a gramicidin, and any salt thereof.

24. The method of claim 20, wherein the antibiotic comprises a penicillin, a methicillin, or a salt thereof.

25. The method of claim 20, wherein the antibiotic comprises an erethromycin, a vancomycin, or a salt thereof.

\* \* \* \* \*